(12) United States Patent
Uchiyama

(10) Patent No.: US 10,368,823 B2
(45) Date of Patent: Aug. 6, 2019

(54) RADIOGRAPHING APPARATUS, CONTROL APPARATUS, CONTROL METHOD, AND STORAGE MEDIUM

(71) Applicant: CANON KABUSHIKI KAISHA, Tokyo (JP)

(72) Inventor: Akehiko Uchiyama, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 370 days.

(21) Appl. No.: 15/007,071

(22) Filed: Jan. 26, 2016

(65) Prior Publication Data

US 2016/0220217 A1  Aug. 4, 2016

(30) Foreign Application Priority Data

Jan. 30, 2015 (JP) .................. 2015-017886
Jan. 30, 2015 (JP) .................. 2015-017889

(51) Int. Cl.
*A61B 6/00* (2006.01)

(52) U.S. Cl.
CPC ............. *A61B 6/5241* (2013.01); *A61B 6/42* (2013.01); *A61B 6/4233* (2013.01); *A61B 6/4266* (2013.01); *A61B 6/4283* (2013.01); *A61B 6/52* (2013.01); *A61B 6/5235* (2013.01); *A61B 6/54* (2013.01); *A61B 6/56* (2013.01); *A61B 6/563* (2013.01); *A61B 6/461* (2013.01); *A61B 6/566* (2013.01)

(58) Field of Classification Search
CPC ....... A61B 6/42; A61B 6/4233; A61B 6/4266; A61B 6/4283; A61B 6/461; A61B 6/52; A61B 6/5235; A61B 6/54; A61B 6/56; A61B 6/563; A61B 6/566; A61B 6/5241

USPC ........ 378/62, 91, 98.8, 98.12, 189; 382/128, 382/132; 250/370.09
See application file for complete search history.

(56) References Cited

U.S. PATENT DOCUMENTS 6,273,606 B1 *  8/2001  Dewaele ............. A61B 6/5241
                                                378/174
6,614,032 B2 *  9/2003  Wendlandt ........... G03B 42/025
                                                206/455
6,696,691 B2 *  2/2004  Foos .................... G03B 42/047
                                                250/484.4
6,793,390 B2 *  9/2004  Wang .................... G06T 3/0075
                                                378/174

(Continued)

FOREIGN PATENT DOCUMENTS

CN       102316806 A    1/2012
JP     2000-258861 A    9/2000

(Continued)

*Primary Examiner* — Allen C. Ho
(74) *Attorney, Agent, or Firm* — Canon U.S.A. Inc., IP Division

(57) ABSTRACT

A radiographing system includes a plurality of radiographic imaging units configured to acquire a plurality of radiographic images, a communication unit to which the plurality of radiographic imaging units is connected, an acquisition unit configured to acquire path information indicating a communication path between each of the plurality of radiographic imaging units connected to the communication unit, and the communication unit, and an output unit configured to output an image acquired from the plurality of radiographic images based on the path information.

31 Claims, 15 Drawing Sheets

(56) References Cited

U.S. PATENT DOCUMENTS

| | | | | |
|---|---|---|---|---|
| 7,247,858 B2* | 7/2007 | De Keyser | | A61B 6/00 250/370.01 |
| 7,250,608 B2* | 7/2007 | Ozeki | | G01T 1/2018 250/370.01 |
| 7,498,583 B2* | 3/2009 | Shoji | | A61B 6/4266 250/370.09 |
| 7,545,914 B2* | 6/2009 | Kito | | A61B 6/4283 378/207 |
| 7,555,100 B2* | 6/2009 | Wang | | A61B 6/02 378/98.12 |
| 7,558,438 B1 | 7/2009 | Sasada | | |
| 7,561,668 B2* | 7/2009 | Ohta | | G03B 42/04 378/102 |
| 7,593,507 B2* | 9/2009 | Ohta | | A61B 6/032 378/207 |
| 7,650,044 B2* | 1/2010 | Kreang-Arekul | | G06T 3/4038 382/128 |
| 7,652,262 B2* | 1/2010 | Ohara | | A61B 6/563 250/390.09 |
| 7,655,916 B2* | 2/2010 | Ohta | | G01T 7/00 250/370.08 |
| 7,732,779 B2* | 6/2010 | Kito | | A61B 6/548 250/370.09 |
| 7,737,427 B2* | 6/2010 | Kito | | A61B 6/4233 250/370.08 |
| 7,740,405 B2* | 6/2010 | Ohta | | H01J 31/49 378/189 |
| 7,751,529 B2* | 7/2010 | Ohara | | A61B 6/00 378/116 |
| 7,787,594 B2* | 8/2010 | Ohta | | A61B 6/4233 378/114 |
| 7,834,322 B2* | 11/2010 | Yoshimi | | A61B 6/4283 250/370.09 |
| 7,847,277 B2* | 12/2010 | Kito | | A61B 6/00 250/580 |
| 7,974,382 B2* | 7/2011 | Kitano | | G01N 23/04 378/114 |
| 7,983,392 B2* | 7/2011 | Venturino | | A61B 6/4283 378/116 |
| 8,107,590 B2* | 1/2012 | Nishino | | A61B 6/00 250/370.09 |
| 8,213,573 B2* | 7/2012 | Liu | | A61B 6/4283 378/62 |
| 8,243,883 B2* | 8/2012 | Omernick | | G01T 7/00 378/116 |
| 8,275,835 B2* | 9/2012 | Eguchi | | A61B 6/4233 709/204 |
| 8,295,439 B2* | 10/2012 | Yonekawa | | A61B 6/00 378/115 |
| 8,319,506 B2* | 11/2012 | Liu | | A61B 6/4283 324/691 |
| 8,351,568 B2* | 1/2013 | Minnigh | | A61B 6/4266 378/204 |
| 8,399,846 B2* | 3/2013 | Niekawa | | A61B 6/4233 250/370.08 |
| 8,401,150 B2* | 3/2013 | Watanabe | | A61B 6/4283 378/114 |
| 8,461,543 B2* | 6/2013 | Nishino | | A61B 6/548 250/370.08 |
| 8,461,544 B2* | 6/2013 | Iwakiri | | G03B 42/04 250/370.09 |
| 8,586,934 B2* | 11/2013 | Nakatsugawa | | G01T 1/2985 250/363.02 |
| 8,625,742 B2* | 1/2014 | Iwashita | | A61B 6/4266 378/116 |
| 8,704,188 B2* | 4/2014 | Kitano | | A61B 6/548 250/370.09 |
| 8,729,484 B2* | 5/2014 | Nishino | | G01T 1/2018 250/370.09 |
| 8,731,141 B2* | 5/2014 | Kuwabara | | A61B 6/00 378/116 |
| 8,748,834 B2* | 6/2014 | Enomoto | | A61B 6/4233 250/370.08 |
| 8,786,257 B2* | 7/2014 | Eguchi | | A61B 6/00 320/127 |
| 8,848,872 B2* | 9/2014 | Lee | | A61B 6/4494 250/370.09 |
| 8,855,691 B2* | 10/2014 | Kamiya | | A61B 6/4283 340/2.1 |
| 8,899,831 B2* | 12/2014 | Yoshida | | A61B 6/4233 250/370.08 |
| 8,975,868 B2* | 3/2015 | Konkle | | H02J 7/0027 320/115 |
| 9,101,316 B2* | 8/2015 | Liu | | A61B 6/4233 |
| 9,131,905 B2* | 9/2015 | Abe | | A61B 6/00 |
| 9,134,436 B2* | 9/2015 | Kwak | | A61B 6/548 |
| 9,168,011 B2* | 10/2015 | Nenoki | | A61B 6/4283 |
| 9,186,118 B2* | 11/2015 | Yonekawa | | A61B 6/4233 |
| 9,216,006 B2* | 12/2015 | Kuwabara | | A61B 6/4233 |
| 9,289,182 B2* | 3/2016 | Yonekawa | | A61B 6/4233 |
| 9,320,482 B2* | 4/2016 | Tajima | | A61B 6/42 |
| 9,402,592 B2* | 8/2016 | Garcia | | A61B 6/4283 |
| 9,492,137 B2* | 11/2016 | Iwamoto | | A61B 6/4283 |
| 9,521,986 B2* | 12/2016 | Ozawa | | A61B 6/4283 |
| 9,538,978 B2* | 1/2017 | Makino | | G16H 40/63 |
| 9,629,591 B2* | 4/2017 | Liu | | A61B 6/4283 |
| 9,649,086 B2* | 5/2017 | Tajima | | A61B 6/563 |
| 9,655,575 B2* | 5/2017 | Park | | A61B 6/4233 |
| 9,661,728 B2* | 5/2017 | Eguchi | | H05G 1/08 |
| 9,668,706 B2* | 6/2017 | Kim | | A61B 6/563 |
| 9,697,923 B2* | 7/2017 | Tsuji | | A61B 6/4266 |
| 9,700,270 B2* | 7/2017 | Tateishi | | A61B 6/44 |
| 9,778,380 B2* | 10/2017 | Enomoto | | G01T 1/161 |
| 9,788,809 B2* | 10/2017 | Hiroike | | A61B 6/54 |
| 9,801,596 B2* | 10/2017 | Tagawa | | A61B 6/4233 |
| 9,820,703 B2* | 11/2017 | Wojcik | | A61B 6/4233 |
| 9,880,111 B2* | 1/2018 | Oda | | H04N 5/32 |
| 9,968,315 B2* | 5/2018 | Ogura | | A61B 6/4283 |
| 10,058,294 B2* | 8/2018 | Tagawa | | A61B 6/4266 |
| 10,058,297 B2* | 8/2018 | Park | | A61B 6/545 |
| 10,104,311 B2* | 10/2018 | Takekoshi | | G06T 7/0012 |
| 2011/0057111 A1 | 3/2011 | Nishino | | |
| 2011/0233415 A1 | 9/2011 | Nakatsugawa et al. | | |
| 2011/0286582 A1 | 11/2011 | Iwashita et al. | | |
| 2012/0049080 A1 | 3/2012 | Enomoto | | |

FOREIGN PATENT DOCUMENTS

| | | |
|---|---|---|
| JP | 2005-257634 A | 9/2005 |
| JP | 2011-224338 A | 11/2011 |
| JP | 2011-227047 A | 11/2011 |
| JP | 2012-45172 A | 3/2012 |
| JP | 2013-226243 A | 11/2013 |

* cited by examiner

RADIOGRAPHING APPARATUS, CONTROL APPARATUS, CONTROL METHOD, AND STORAGE MEDIUM

BACKGROUND OF THE INVENTION

Field of the Invention

The present invention relates to a radiographing system using a plurality of radiographic imaging units.

Description of the Related Art

As one of image-capturing methods using a radiographic imaging unit, such as a film cassette, an imaging plate based on the Computed Radiography (CR) method, or a digital radiation detector, there is long-scale imaging for capturing a larger subject than a region where a single radiographic imaging unit detects radiation.

Methods for implementing the long-scale imaging include a method that lays out a plurality of radiographic imaging units and irradiates the subject with a single shot of radiation, besides a method that irradiates the subject with a plurality of shots of radiation while moving a single radiographic imaging unit. A plurality of radiographic images acquired by any of these methods is appropriately arranged and spliced, by which an image of the larger subject than the region where the single radiographic imaging unit detects radiation can be acquired.

However, the use of the plurality of radiographic imaging units leads to, for example, a lot of time and effort spent on processing for splicing the radiographic images acquired from the plurality of radiographic imaging units to generate the long-scale image if a layout among the radiographic imaging units is unknown.

SUMMARY OF THE INVENTION

According to an aspect of the present invention, a radiographing system includes a plurality of radiographic imaging units configured to acquire a plurality of radiographic images, a communication unit to which the plurality of radiographic imaging units is connected, an acquisition unit configured to acquire path information indicating a communication path between each of the plurality of radiographic imaging units connected to the communication unit, and the communication unit, and an output unit configured to output an image acquired from the plurality of radiographic images based on the path information.

Further features of the present invention will become apparent from the following description of exemplary embodiments with reference to the attached drawings.

DESCRIPTION OF THE EMBODIMENTS

Figure 1:
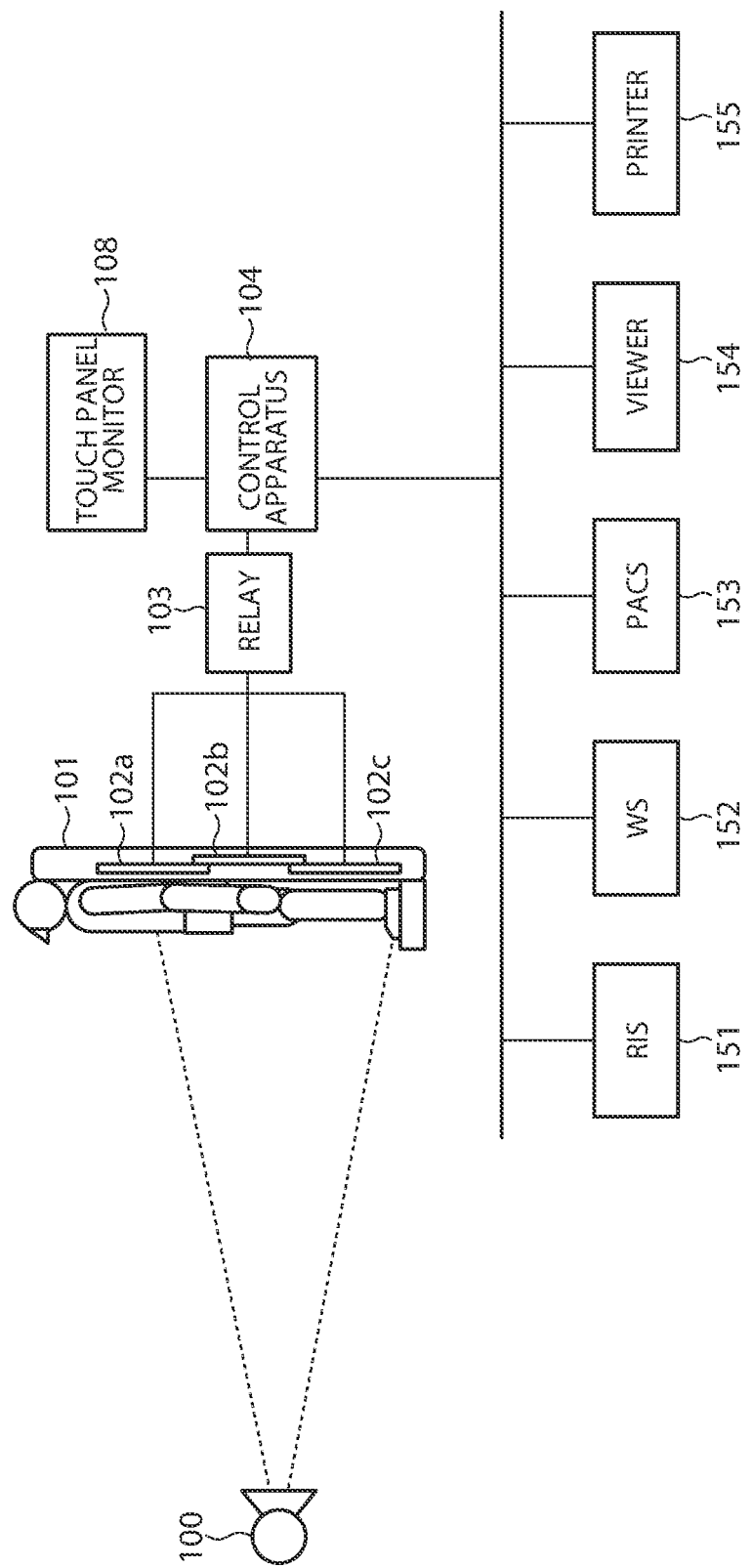
FIG. 1 is a block diagram illustrating a configuration of an information system including a radiographing system according to an exemplary embodiment.

A radiographing system according to an exemplary embodiment will be described with reference to FIG. 1. FIG. 1 illustrates a configuration of an information system including a long-scale imaging system using an X-ray as radiation, which is an example of the radiographing system. This information system includes, for example, the radiographing system, a radiology information system (RIS) 151, a workstation (WS) 152, a picture archiving and communication system (PACS) 153, a viewer 154, and a printer 155. The RIS 151 is a system that manages an order for radiographic imaging, and transmits the order for radiographic imaging to the radiographing system. The WS 152 is an image processing terminal, and processes a radiographic image captured by the radiographing system to acquire an image for use in diagnosis. The PACS 153 is a database system that contains medical images provided from the radiographing system and another modality (a medical imaging system or a medial image-capturing apparatus). The PACS 153 includes a storage unit that stores the medical images and appendant information, such as image-capturing conditions applied for these medical images, and a controller that manages the information stored in this storage unit. The viewer 154 is a terminal for use in image diagnosis, and reads out the image stored in the PACS 153 or the like to display this image for the diagnosis. The printer 155 is, for example, a film printer, and outputs the image stored in the PACS 153 onto a film.

The long-scale imaging system, which is an example of the radiographing system, includes a radiation generation unit 100, a platform 101, a plurality of radiographic imaging units 102*a*, 102*b*, and 102*c* (or a cassette A, a cassette B, and a cassette C), a relay 103, a control apparatus 104, and a touch panel monitor 108 that serves as both a display unit and an operation unit. These components are connected to one another via a cable. The radiation generation unit 100 emits the radiation to the plurality of radiographic imaging units 102*a*, 102*b*, and 102*c* simultaneously for irradiation.

When the radiation is emitted to the plurality of radiographic imaging units 102a, 102b, and 102c for the irradiation, the plurality of radiographic imaging units 102a, 102b, and 102c acquires radiographic images, and this plurality of radiographic images is transmitted to the control apparatus 104 via the relay 103.

The control apparatus 104 is, for example, an electronic computer (a personal computer (PC)) with a desired software program installed therein, and generates a long-scale image by performing image processing including splicing processing on this plurality of radiographic images. Further, the control apparatus 104 causes this long-scale image to be displayed on the touch panel monitor 108. In this manner, the long-scale imaging system carries out the long-scale imaging of emitting the radiation to the plurality of radiographic imaging units 102a, 102b, and 102c simultaneously for the irradiation. Further, the control apparatus 104 generates a Digital Imaging and Communications in Medicine (DICOM) image based on this long-scale image and appendant information, such as an image-capturing condition applied for this long-scale image. Then, the control apparatus 104 transmits this DICOM image to the WS 152 or the PACS 153.

An image-capturing order for the long-scale imaging is, for example, transmitted from the RIS 151 to the control apparatus 104. In this case, the control apparatus 104 receives, from the RIS 151, an image-capturing information identification (ID) indicating the long-scale imaging, and information indicating an image-capturing site that should be captured by the long-scale imaging, such as an entire lower limb and an entire spine, and reads out an image-capturing condition corresponding to this received information from a storage unit of the control apparatus 104. Alternatively, the control apparatus 104 may be assumed to acquire image-capturing information including information indicating the image-capturing site, an image-capturing method, and the image-capturing condition from an operation input via the touch panel monitor 108.

Besides the touch panel monitor 108, an operation unit such as a mouse and a keyboard may be connected to the control apparatus 104.

As illustrated in FIG. 1, the plurality of radiographic imaging units 102a, 102b, and 102c are laid out in such a manner that a region that the radiographic imaging unit 102a captures and a region that the radiographic imaging unit 102b captures partially overlap each other so as to establish a continuous imaging region. This layout results in the appearance of a predetermined structure in the radiographic image acquired by the radiographic imaging unit 102b. On the platform 101 according to the present exemplary embodiment, only a radiographic imaging unit 102c disposed in the middle among the plurality of radiographic imaging units 102a, 102b, and 102c disposed in the order is located at a position farther away from the radiation generation unit 100 than the other radiographic imaging units 102a, 102b, and is arranged in such a manner that the imaging region thereof partially overlaps the imaging regions of the other radiographic imaging units 102a, 102b. Laying out the plurality of radiographic imaging units 102a, 102b, and 102c in this manner can reduce the number of radiographic images with the structure appearing therein.

The radiographic image with the structure appearing therein is corrected by, for example, the control apparatus 104 or one of the plurality of radiographic imaging units 102a, 102b, 102c with use of correction data for correcting the structure that is separately acquired, so that the number of structures appearing in the radiographic image(s) is reduced.

Figure 2:
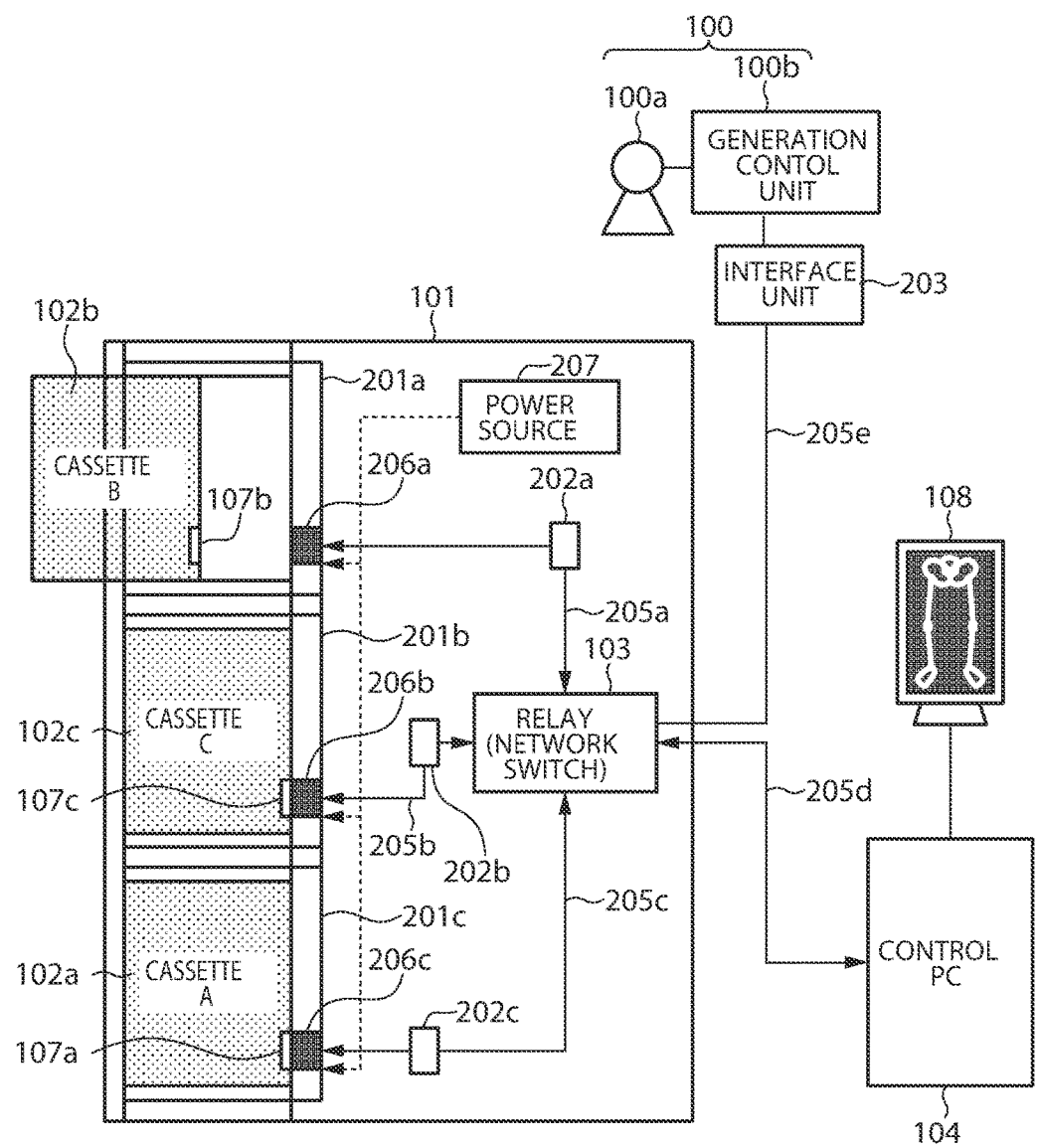
FIG. 2 is a block diagram illustrating a configuration of a long-scale imaging system according to the exemplary embodiment.

A configuration of the long-scale imaging system according to the present exemplary embodiment will be described in detail with reference to FIG. 2. The radiation generation unit 100 includes a radiation irradiation unit 100a that includes a diaphragm for setting a range to be irradiated with the radiation and a radiation source for generating the radiation, and a generation control unit 100b for controlling the irradiation with the radiation by the radiation irradiation unit 100a. An irradiation switch is further connected to the generation control unit 100b to input a signal for instructing the generation control unit 100b about a timing of starting the irradiation to the generation control unit 100b. The radiation generation unit 100 may further include an interface unit 203 that communicates with the plurality of radiographic imaging units 102a, 102b, and 102c. In this case, the radiation generation unit 100 and the platform 101 are connected communicably with each other via a network cable 205e, such as an Ethernet (registered trademark) cable. The control apparatus 104 is connected to the platform 101 communicably with each other via a network cable 205d.

The platform 101 is a holder unit that fixes the plurality of radiographic imaging units 102a, 102b, and 102c for carrying out the long-scale imaging. In one exemplary embodiment, the platform 101 has three positions for fixing the plurality of radiographic imaging units 102a, 102b, and 102c, and includes a housing portion 201a that houses the radiographic imaging unit 102b, and a platform connector 206a at the fixation position. The position of each of the platform connectors 206a, 206b, 206c is determined in such a manner that each of the platform connectors 206a, 206b, 206c and each of the radiographic imaging unit connectors 107a, 107b, 107c are fitted to each other when each of the radiographic imaging units 102a, 102b, 102c is fixed in each of the housing portions 201a, 201b, 201c respectively.

The platform 101 includes housing portions 201a, 201b, and 201c that house the plurality of radiographic imaging units 102a, 102b, and 102c, respectively, platform connectors 206a, 206b, and 206c respectively disposed along sidewalls of the housing portions 201a, 201b, and 201c and respectively provided for establishing wired connections with the plurality of radiographic imaging units 102a, 102b, and 102c, and the relay 103 (a network switch).

The platform connectors 206a, 206b, and 206c are connected to the relay 103 via network cables 205a, 205b, and 205c, respectively. Further, the platform connectors 206a, 206b, and 206c are connected to the radiographic imaging unit connectors 107a, 107b, 107c of the radiographic imaging units 102a, 102b, and 102c, respectively. In the example illustrated in FIG. 2, a radiographic imaging unit connector 107b of the radiographic imaging unit 102b, a radiographic imaging unit connector 107c of the radiographic imaging unit 102c, and a radiographic imaging unit connector 107a of the radiographic imaging unit 102a are connected to the platform connector 206a, the platform connector 206b, and the platform connector 206c, respectively.

The relay 103 is the network switch, and one of a plurality of physical ports thereof is extended out of the platform 101 so as to be connectable to the control apparatus 104. This port is fixedly wired so as to be connected to a communication port of the control apparatus 104, when the platform 101 and the control apparatus 104 are set up in a user's use environment. The remaining ports are wired so as to be connected to the platform connectors 206a, 206b, and 206c at the cassette fixation positions. This wiring is fixedly wired when the platform 101 is manufactured, so that corresponding relationships between the platform connectors 206a, 206b, and 206c and the physical ports of the relay 103 do not change over the course of the user's use.

The platform 101 may further include a power source 207 that supplies power to the radiographic imaging units 102a, 102b, and 102c. This configuration leads to connections of two cable systems, a network cable and a power source cable to each of the platform connectors 206a, 206b, and 206c. Instead of the power source unit 207, power source units 202a, 202b, and 202c may be provided with respect to the housing portions 201a, 201b, and 201c, respectively. This configuration leads to connections of two systems, a communication cable and a power source cable between each of the platform connectors 206a, 206b, 206c and the power source unit 202, and a connection of a communication cable between the power source unit 202 and the relay 103.

The radiographic images provided from the radiographic imaging units 102a, 102b, and 102c are transmitted to the control apparatus 104 via the radiographic imaging unit connectors 107a, 107b, and 107c, the platform connectors 206a, 206b, and 206c, and the relay 103.

In another exemplary embodiment, the platform 101 may be configured to include a radiographic imaging unit connection portion and a platform connection portion that perform near field wireless communication, such as TransferJet, instead of each of the radiographic imaging unit connectors 107a, 107b, 107c and each of the platform connectors 206a, 206b, 206c. Alternatively, each of the radiographic imaging units 102a, 102b, 102c may be configured to wirelessly communicate with the relay 103 directly without communicating via each of the platform connectors 206a, 206b, 206c and the like. This configuration leads to each of the radiographic imaging units 102a, 102b, 102c wirelessly communicating with the platform 101 and the relay 103, and makes the communication path partially wireless between each of the radiographic imaging units 102a, 102b, 102c and the control apparatus 104.

The relay 103 is disposed inside the platform 101, but is not limited thereto and may be disposed outside the platform 101. Further, the relay 103 and the radiation generation unit 100 may be connected to each other via a wireless communication path, and the relay 103 and the control apparatus 104 may be connected to each other via a wireless communication path.

To carry out the long-scale imaging, first, the radiographic imaging units 102a, 102b, and 102c are fixedly mounted onto the respective fixation positions of the platform 101 provided for the long-scale imaging. By this mounting, the platform connectors 206a, 206b, and 206c and the radiographic imaging unit connectors 107a, 107b, and 107c are fitted to each other, respectively. By this fitting, respective main control circuits inside the individual radiographic imaging units 102a, 102b, and 102c are connected to the relay 103 via the radiographic imaging unit connectors 107a, 107b, and 107c, the platform connectors 206a, 206b, and 206c, and the network cables 205a, 205b, and 205c, respectively. As a result, a network including the individual radiographic imaging units 102a, 102b, and 102c and the control apparatus 104 is created. The radiographic imaging units 102a, 102b, and 102c and the relay 103 are connected in an individually attachable and detachable manner by the fitted attachment between the radiographic imaging unit connectors 107a, 107b, and 107c and the platform connectors 206a, 206b, and 206c.

The creation of the network allows each of the cassettes A, B, and C and the control apparatus 104 to communicate with each other, thereby causing the software of the control apparatus 104 to start control communication with each of the cassettes A, B, and C. This control communication allows the software of the control apparatus 104 to recognize that each of the radiographic imaging units 102a, 102b, and 102c is mounted on the platform 101, and also recognize a position where each of the cassettes A, B, and C is mounted on the holder. How the position recognition proceeds will be described below.

When the user completes the operation of mounting the radiographic imaging units 102a, 102b, and 102c, and the software can confirm that the radiographic imaging units 102a, 102b, and 102c are mounted normally, the software displays the completion of the preparation on the touch panel monitor 108 connected to the control apparatus 104. The user confirms the display indicating the completion of the preparation, and carries out the image-capturing. As illustrated in FIG. 1, the image-capturing is carried out in such a manner that a subject is positioned in front of the platform 101, and the subject in a wide range extending across the plurality of radiographic imaging units 102a, 102b, and 102c can be imaged by being irradiated with the radiation a single time.

After the image-capturing is carried out, a main control circuit 150 of each of the cassettes A, B, and C generates image data by scanning a two-dimensional image sensor 120. The generated image data is transferred to the control apparatus 104. In this case, the image data may be transferred with use of a communication path via a wired communication circuit 180 and each of the radiographic imaging unit connectors 107a, 107b, 107c built in each of the radiographic imaging units 102a, 102b, 102c, each of the platform connectors 206a, 206b, 206c, and the like. Alternatively, the image data may be transferred via a wireless communication circuit 160 built in each of the radiographic imaging units 102a, 102b, 102c, and a not-illustrated wireless access point connected to the control apparatus 104.

The control apparatus 104 performs image processing for rearranging the images received from the individual radiographic imaging units 102a, 102b, and 102c by referring to recognized information about the positions where the cassettes A, B, and C are mounted, and connectively combines them. The combined image is presented to the user as a long-scale imaging image that contains information of the subject in the wide range.

Figure 3:
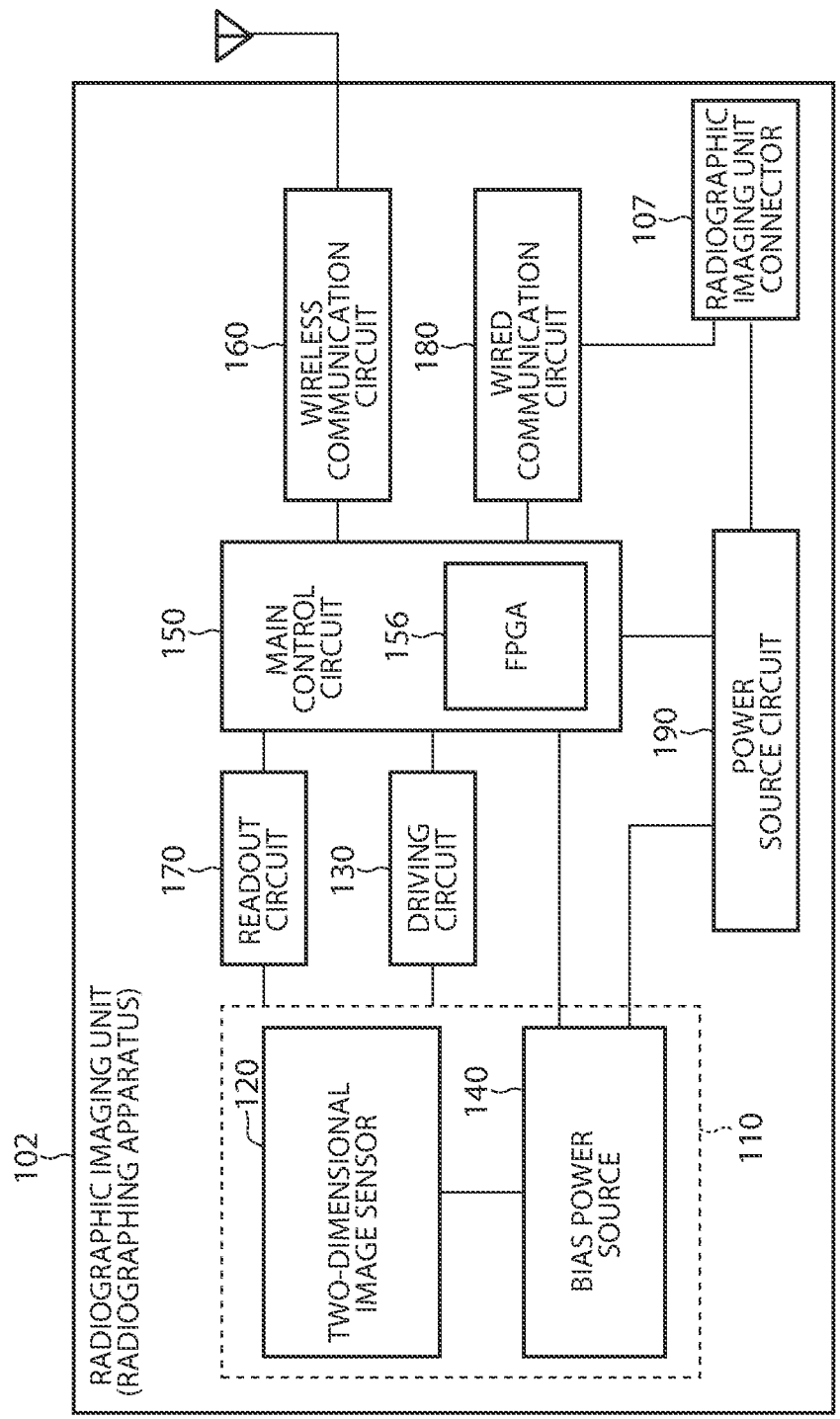
FIG. 3 is a block diagram illustrating a configuration of a radiographic imaging unit according to the exemplary embodiment.

A configuration of each of the plurality of radiographic imaging units (a radiographing apparatus) 102a, 102b, 102c according to the present exemplary embodiment will be described with reference to FIG. 3. Each of the plurality of radiographic imaging units 102a, 102b, 102c includes a radiation sensor 110, a driving circuit 130, a readout circuit 170, the main control circuit 150, the wireless communication circuit 160, the wired communication circuit 180, each of the radiographic imaging unit connectors 107a, 107b, 107c, and a power source circuit 190. The radiation sensor 110 includes the two-dimensional image sensor 120. The two-dimensional image sensor 120 includes a pixel array in which a plurality of pixels is arrayed in the form of a matrix, a row selection line that is commonly connected to pixels lined up in a row direction and transmits a driving signal issued from the driving circuit 130, and a column signal line that is commonly connected to pixels lined up in a column direction and transmits an image signal to the readout circuit 170. A bias power source 140 is connected to each of the pixels of the two-dimensional image sensor 120. The pixels each include a photoelectric conversion element having one end connected to the bias power source 140, and a switching element connected to another end of this photoelectric conversion element. A base electrode of the switching element is connected to the row selection line, and the photoelectric conversion element and the column signal line are connected to a collector and an emitter of the switching element. The two-dimensional image sensor 120 generates the image based on a distribution of intensity of the radiation incident on this image sensor 120.

Other than those, the radiation sensor 110 may include a binning circuit that includes a switching element for connecting a plurality of pixels to one another, and combines image signals. For example, the switching element is connected to four pixels, vertically adjacent two pixels and horizontally adjacent two pixels. This configuration allows the radiation sensor 110 to combine the image signals before the image signals are digitized.

The driving circuit 130 controls an on state and an off state of the switching element by outputting the driving signal. When the switching element is controlled into the off state, this causes the image signal to be stored into a parasitic capacitance or the like of the photoelectric conversion element. When the switching element is controlled into the on state, this causes the stored image signal to be output via the column signal line. The readout circuit 170 includes an amplifier for amplifying the image signal output from the radiation sensor 110, and an analog-to-digital (A/D) converter for converting the image signal into a digital signal. The image signal is read out as the digital signal by them.

The driving circuit 130 performs control of collectively applying off-state voltages and control of sequentially applying on-state voltages to the row selection lines corresponding to the individual rows of the pixel array. The off-state voltages cause the radiation sensor 110 to transition to a storage state. The control of sequentially applying the on-state voltages causes the signals of the pixel array to be sequentially output to the readout circuit 170. By theses control procedures, each of the plurality of radiographic imaging units 102a, 102b, 102c performs an operation of initializing the pixel array before causing the radiation sensor 110 to transition to the storage state, and an operation of reading out the image signals acquired from the storage.

The driving circuit 130 may conduct interlace driving of sequentially applying the on-state voltages to 2n rows, i.e., even-numbered rows, and then sequentially applying the on-state voltages to 2n−1 rows, i.e., odd-numbered rows after that. By this driving, the driving circuit 130 realizes reading out the image signals while thinning out the image signals. The thinning-out driving is not limited to the method that conducts this driving at intervals of one row as described above, and may be set to be conducted at intervals of two rows or m−1 rows. A desired value is adopted as a rate at which the image signals are thinned out in this manner. The driving circuit 130 may be set to sequentially apply the on-state voltages, like sequentially applying the on-state voltages to an mn row, an mn+1 row, an mn+2 row, . . . and an mn+(m−1) row, when m−1 is set as the rate at which the image signals are thinned out.

Alternatively, the driving circuit 130 can also conduct partial readout of the image signals, which means outputting image signals acquired from pixels around a center of the pixel array prior to the other image signals. In this case, supposing that the pixel array is constituted by M rows and N columns, M/2×N/2 image signals of an M/4+1 row to a 3M/4 row and an N/4+1 column to a 3N/4 column are output. The above-described operations performed by the driving circuit 130 are performed according to control from the main control circuit 150.

The main control circuit 150 integrally controls each of the plurality of radiographic imaging units 102a, 102b, 102c. Further, the main control circuit 150 includes a processing circuit implemented by a field-programmable gate array (FPGA) 156, and generates the radiographic image and performs the image processing thereby. The FPGA 156 can perform processing for acquiring an image small in data amount by, for example, the binning processing that sums up values of the adjacent 2×2 pixels, the thinning-out processing that partially thins out the pixels and partially extracts the pixels, or processing that extracts a continuous region, when acquiring the digital radiographic image.

Further, examples of the image processing that may be performed by the FPGA 156 include a dark correction for reducing a dark current component in the radiographic image, a gain correction for correcting a variation in an input/output characteristic of the pixel, a correction of a defective pixel, and processing for reducing a noise, such as a line noise.

The wireless communication circuit 160 and the wired communication circuit 180 can transmit and receive a control command and data, such as a signal from the control apparatus 104 and the radiation generation unit 100. Further, the wireless communication circuit 160 transmits a signal indicating a state of each of the plurality of radiographic imaging units 102a, 102b, 102c, and the radiographic image. The wireless communication circuit 160 includes an antenna, and performs wireless communication mainly when the wired cable 205 is not connected to each of the radiographic imaging unit connectors 107a, 107b, 107c. Each of the radiographic imaging unit connectors 107a, 107b, 107c is connected to the wired communication circuit 180, and the wired communication circuit 180 controls the wired communication. Each of the radiographic imaging unit connectors 107a, 107b, 107c is provided for the communication and the power supply, and the communicated information and the power are transmitted to the wired communication circuit 180 and the power source circuit 190, respectively. The power source circuit 190 includes a battery, and produces a voltage required for the operation of each of the plurality of radiographic imaging units 102a, 102b, 102c to supply the voltage to each of the units. The main control circuit 150 specifies which communication method should be used, the wireless communication or the wired communication. For example, the wired communication is specified if the wired cable 205 is connected to each of the radiographic imaging unit connectors 107a, 107b, 107c, and the wireless communication is specified if the wired cable 205 is not connected but a connection via the wireless communication is established. Neither communication method is specified if the wired cable 205 is not connected and a connection via the wireless connection is also not established. In this case, for example, the radiographic image is not transmitted, and is stored into a nonvolatile memory connected to the main control circuit 150.

If transmitting the radiographic image with any of the communication methods specified, the main control circuit 150 transfers a preview image smaller in data amount than the radiographic image acquired by the radiation sensor 110 prior to this radiographic image. Then, the main control circuit 150 transmits an image that contains data uncontained in the preview image after completion of the transmission of this preview image.

This transmission allows the control apparatus 104 side to quickly check whether the image-capturing has been appropriate. The preview image and the image that contains the data uncontained in the preview image may be transmitted according to the readout of the image signals by the readout circuit 170 and the generation of the preview image by the main control circuit 150. Alternatively, the main control circuit 150 may be set to transmit these images according to a signal from the control apparatus 104. In this manner, the control apparatus 104 controls the communication with the plurality of radiographic imaging units 102a, 102b, and 102c, which can reduce an influence due to simultaneous transmission of large-volume data from the plurality of radiographic imaging units 102a, 102b, and 102c, thereby realizing efficient image communication.

Because this influence on the communication can be less likely to arise in some cases, for example, when each of the radiographic imaging units 102a, 102b, 102c is connected to the control apparatus 104 via the wired communication or the communication capacity is sufficiently large, the main control circuit 150 may be configured to change the method for transmitting the images according to the communication method between the control apparatus 104 and each of the plurality of radiographic imaging units 102a, 102b, 102c.

One of states of each of the plurality of radiographic imaging units 102a, 102b, 102c is a first state in which power is supplied only to the wireless communication circuit 160 and the wired communication circuit 180, and no power is supplied from the bias power source 140 to the two-dimensional image sensor 120 (a so-called sleep state). Further, another state of each of the plurality of radiographic imaging units 102a, 102b, 102c is a second state in which power is supplied from the bias power source 140 to the two-dimensional image sensor 120. In the second state, the initialization operation is conclusively performed, and each of the plurality of radiographic imaging units 102a, 102b, 102c is ready to generate the image by transitioning to the storage state in response to an instruction from outside. Each of the plurality of radiographic imaging units 102a, 102b, 102c transmits the signal indicating the above-described state according to a request signal from outside.

In a case where the radiation generation unit 100 is provided with the interface unit 203, synchronized communication is performed between the radiation generation unit 100 and each of the plurality of radiographic imaging units 102a, 102b, 102c. In response to pressing of the irradiation switch, the interface unit 203 transmits a first signal to each of the radiographic imaging units 102a, 102b, and 102c. According to this first signal, the driving circuit 130 of each of the radiographic imaging units 102a, 102b, and 102c causes the two-dimensional image sensor 120 to perform the initialization operation, and to transition to the storage state. Upon completion of the initialization and the transition to the storage state, each of the radiographic imaging units 102a, 102b, and 102c transmits a second signal to the interface unit 203. The interface unit 203 determines whether the second signals are received from all of radiographic imaging units 102 to be used for a certain long-scale imaging, and inputs a signal for permitting the irradiation to the generation control unit 100b if the interface unit 203 has determined that the second signals are received from all of them. According thereto, the radiation is emitted from the radiation irradiation unit 100a for the irradiation. Controlling the units in this manner can prevent the radiation irradiation from being carried out before the radiographic imaging units 102a, 102b, and 102c transition to the storage state, thereby reducing unnecessary exposure.

In a case where the radiation generation unit 100 is not provided with the interface unit 203, the radiation generation unit 100 irradiates the subject with the radiation in response to the pressing of the irradiation switch. Each of the radiographic imaging units 102a, 102b, and 102c detects this start of the radiation irradiation, and transitions to the storage state. The radiographic imaging unit 102a, 102b, and 102c may each detect the start of the irradiation based on a signal acquired by the two-dimensional image sensor 120, or may detect the start of the irradiation by a sensor for detecting the start of the irradiation that is provided separately from the radiation sensor 110.

The main control circuit 150 specifies which mode should be employed, a first image-capturing mode of performing the synchronized communication or a second image-capturing mode of detecting the radiation, according to a signal input from outside.

Figure 4:
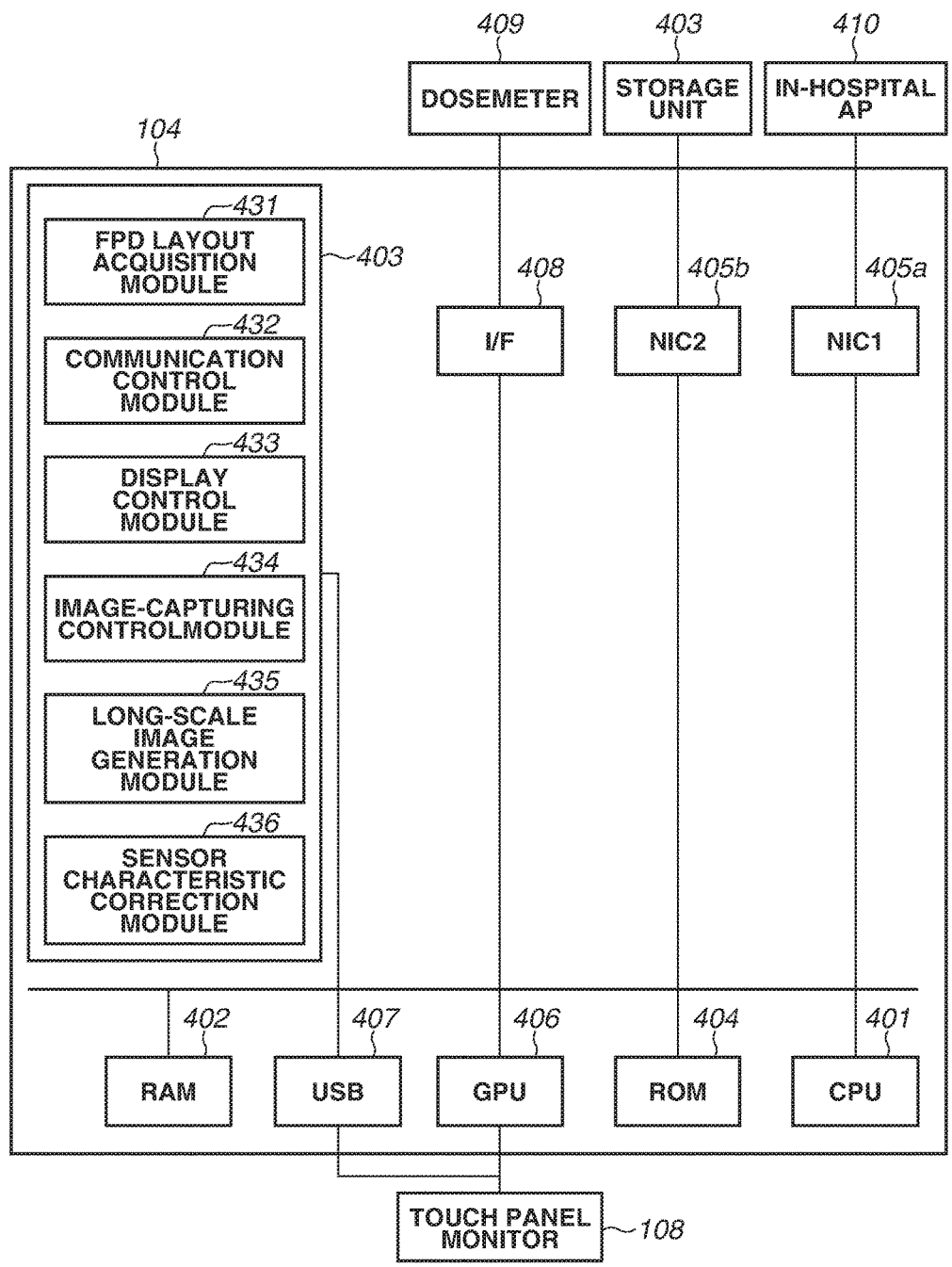
FIG. 4 is a block diagram illustrating a configuration of a control apparatus according to the exemplary embodiment.

A configuration of the control apparatus 104 according to the present exemplary embodiment will be described with reference to FIG. 4. The control apparatus 104 includes a central processing unit (CPU) 401, a random access memory (RAM) 402, a storage unit 403, a read only memory (ROM) 404, network interface cards (NICs) 405 (405a and 405b), a graphic processing unit (GPU) 406, a universal serial bus (USB) interface 407, and a communication interface (I/F) 408. These components are communicably connected to one another via an internal bus. The CPU 401 is a control circuit that comprehensively controls the control apparatus 104 and each of units connected to the control apparatus 104, and may include a plurality of CPUs. The RAM 402 is a memory used for loading a program for performing, for example, processing illustrated in FIG. 6 that will be described below, and various kinds of parameters, which are stored in the storage unit 403 or the like. The CPU 401 sequentially executes commands contained in the program loaded into this RAM 402, by which the processing according to the present exemplary embodiment is realized. The storage unit 403 is a memory such as a hard disk drive (HDD) and a solid state drive (SSD), and stores the above-described program, the radiographic image such as the long-scale image acquired by the image-capturing, the image-capturing order, the image-capturing information, and in addition thereto, the various kinds of parameters. The NICs 405 are an example of a communication unit that communicates with an external apparatus. The control apparatus 104 according to the present exemplary embodiment includes a first NIC 405a and a second NIC 405b. The first NIC 405a is connected to an in-hospital access point (AP) 410 for connecting to an in-hospital network, and the second NIC 405b is connected to the relay 103 that relays the communication of the radiographing system. The GPU 406 is an image processing unit, and performs the image processing according to control from the CPU 401. An image acquired as a result of the image processing is output and displayed onto the touch panel monitor 108. The USB I/F 407 is a communication unit that acquires information relating to an operation input from the touch panel monitor 108, and is interpreted as the operation input by the CPU 401. The communication I/F 408 is, for example, a communication unit supporting a standard such as Recommended Standard 232 version C (RS232C), Ethernet (registered trademark), and USB, and communicates with a dosemeter (a dose measurement device) 409 to receive information indicating a radiation dose.

The program stored in the storage unit 403 includes, for example, a flat panel detector (FPD) (radiographic imaging unit) layout acquisition module 431, a communication control module 432, a display control module 433, an image-capturing control module 434, a long-scale image generation module 435, and a correction module 436.

The FPD layout acquisition module 431 acquires information indicating a layout relationship among the plurality of radiographic imaging units 102a, 102b, and 102c to be used to carry out the one long-scale imaging. The information indicating the layout relationship is, for example, information indicating that the radiographic imaging units 102a, 102b, and 102c are laid out so as to be arranged in this order, or information indicating that the radiographic imaging unit 102b is located in the middle of them. The information indicating the layout relationship may contain information indicating rotational states of the radiographic imaging units 102a, 102b, and 102c. Such information indicating the layout relationship is acquired by the CPU 401 based on, for example, information, received by the second NIC 405b, indicating the communication paths of the radiographic imaging units 102a, 102b, and 102c, and correspondence information, stored in the storage unit 403, indicating correspondence relationships between the communication paths and the layout positions. For example, in a case where the platform connectors 206a, 206b, and 206c are disposed fixedly relative to the housing portions 201a, 201b, and 201c as illustrated in FIG. 2, the layout positions of the plurality of radiographic imaging units 102a, 102b, and 102c can be identified by referring to the information indicating the communication paths. For example, in a case where the relay 103 is a layer 2 network switch, the relay 103 performs an operation of learning relationships between the physical ports and media access control (MAC) addresses, and correspondence relationships between the radiographic imaging units 102a, 102b, and 102c and the physical ports are acquired as the information indicating the communication paths with use of this operation.

This information indicating the layout relationships acquired in this manner is stored into the storage unit 403. Alternatively, the second NIC 405b may receive the information indicating the layout relationship. In this case, the relay 103 or the platform 101 is assumed to have a function of acquiring the information indicating the layout relationship based on the information indicating the communication paths and the like.

The information indicating the layout relationship is, for example, referred to during the course of execution of the long-scale image generation module 435, and used in the processing for splicing the plurality of radiographic images. The information indicating the layout relationship in this case is information for identifying which radiographic images contain an overlap region therebetween. Further, the information indicating the layout relationship is, for example, referred to by the CPU 401 to determine which radiographic image should be subjected to execution of the correction processing for removing the structure appearing therein during the course of execution of the correction module 436. The information indicating the layout relationship in this case is information for identifying which one of the radiographic imaging units 102a, 102b, and 102c has output the image with the structure appearing therein, and corresponds to information for identifying which one of the radiographic imaging units 102a, 102b, and 102c radiographic imaging unit is located in the middle of the radiographic imaging units 102a, 102b, and 102c in the imaging system illustrated in FIG. 1.

The communication control module 432 controls the communication by the first NIC 405a and the second NIC 405b. Execution of the communication control module 432 causes, for example, the control apparatus 104 to transmit the signals for causing the states of the plurality of radiographic imaging units 102a, 102b, and 102c to transition to the second state to the radiographic imaging units 102a, 102b, and 102c according to an operation input from the touch panel monitor 108 or the like. This operation input is carried out, for example, according to an operation input for selecting one of a plurality of image-capturing conditions contained in the image-capturing order and then the CPU 401 specifying this image-capturing condition based thereon. In response to this operation input, the second NIC 405b transmits the signals for causing the states to transition, to the radiographic imaging units 102a, 102b, and 102c. Then, the second NIC 405b will receive response signals thereto.

Further, the execution of the communication control module 432 causes, for example, the control apparatus 104 to receive the radiographic image from each of the plurality of radiographic imaging units 102a, 102b, and 102c. At this time, the control apparatus 104 is assumed to first receive the preview image (a first image) small in data amount and then receive the image that contains the remaining data (a second image) after that, from each of the plurality of radiographic imaging units 102a, 102b, and 102c. In this case, the control apparatus 104 is assumed to, when receiving the preview image (the first image) from one radiographic imaging unit 102, restrict the reception of the first or second image from the other radiographic imaging units 102. Therefore, each of the radiographic imaging units 102a, 102b, and 102c is assumed to be set to transmit the image according to an instruction from the control apparatus 104, and the control apparatus 104 is assumed to instruct one radiographic imaging unit 102 to transmit the second image according to, for example, completion of the reception of the preview images (the first images) from all of the radiographic imaging units 102a, 102b, and 102c. By this control, the large-volume data is prevented from being transmitted from the plurality of radiographic imaging units 102a, 102b, and 102c to the relay 103 simultaneously, thereby improving efficiency of the communication.

The radiographic imaging unit side can also perform a transmission method in which the radiographic image is transmitted in response to the readout of the image signals (a first transmission method), besides the transmission method in which the image is transmitted in response to the instruction signal as described above (a second transmission method). The transmission method to be performed is, for example, specified according to a signal from the control apparatus 104. For example, the first transmission method is specified in the case where each of the plurality of radiographic imaging units 102a, 102b, 102c performs the wired communication, and the second transmission method is specified in the case where each of the plurality of radiographic imaging units 102a, 102b, 102c performs the wireless communication. In the case where the transmission method is specified according to the communication configuration in this manner, each of the plurality of radiographic imaging units 102a, 102b, 102c can specify the transmission method regardless of the signal from outside.

Besides that, by executing the communication control module 432, the CPU 401 cause a DICOM image file containing the radiographic image acquired by the radiographic imaging or the long-scale imaging to be transmitted to the PACS 153 via the first NIC 405a.

In one exemplary embodiment, the FPGA 156 of each of the plurality of radiographic imaging units 102a, 102b, 102c performs the processing for correcting the structure appearing in the radiographic image. In this case, the CPU 401 specifies each of the plurality of radiographic imaging units 102a, 102b, 102c to be instructed to perform the processing for correcting the structure among the plurality of radiographic imaging units 102a, 102b, and 102c during the course of the execution of the communication control module 432. As an example thereof, the radiographic imaging unit 102b located in the middle of the radiographic imaging units 102a, 102b, and 102c illustrated in FIG. 1 is specified with use of the information indicating the layout relationship. Then, the CPU 401 causes the second NIC 405b to transmit an instruction signal for instructing the radiographic imaging unit 102b to perform the processing for correcting the structure to the radiographic imaging unit 102b.

The display control module 433 is used in processing for controlling a content of a display screen displayed on the touch panel monitor 108. This processing is, for example, processing for displaying the image-capturing condition corresponding to the long-scale imaging and processing for displaying the generated long-scale image on the display screen. Further, by this module, the CPU 401 determines whether any one of the above-described plurality of radiographic imaging units 102a, 102b, and 102c is in the first state or all of the above-described plurality of radiographic imaging units 102a, 102b, and 102c are in the second state based on the information indicating the respective states of the plurality of radiographic imaging units 102a, 102b, and 102c. Then, the CPU 401 controls the display of the touch panel monitor 108 according to this determination. The second NIC 405b receives the state information indicating whether each of the plurality of radiographic imaging units 102a, 102b, 102c is in the first state, which is not a state prepared for the acquisition of the radiographic image, or the second state, which is the state prepared for the acquisition of the radiographic image, with respect to each of the plurality of radiographic imaging units 102a, 102b, and 102c. The CPU 401 determines whether any one of the above-described plurality of radiographic imaging units 102a, 102b, and 102c is in the first state or all of the above-described plurality of radiographic imaging units 102a, 102b, and 102c are in the second state.

Controlling the display in this manner allows the control apparatus 140 to present a display indicating whether all of the radiographic imaging units 102a, 102b, and 102c are in the state capable of the image-capturing, instead of a display individually indicating the state of each of the radiographic imaging units 102a, 102b, and 102c, thereby allowing the user to intuitively recognize whether the long-scale imaging can be carried out. Alternatively, the control apparatus 104 may also be configured to present the display individually indicating the state of each of the radiographic imaging units 102a, 102b, and 102c, together with the display indicating whether all of the radiographic imaging units 102a, 102b, and 102c are in the state capable of the image-capturing, and it is apparent that such a display allows the user to readily take some measures, for example, when one radiographic imaging unit 102 cannot carry out the image-capturing due to an error.

The image-capturing control module 434 is a program for causing the CPU 401 to integrally control the execution of the radiographic imaging including the long-scale imaging. By the image-capturing control module 434, for example, the CPU 401 specifies the image-capturing condition according to the operation input, transmits the signal for requesting the state of each of the units of each of the plurality of radiographic imaging units 102a, 102b, 102c, and controls the reception of the radiographic images.

The long-scale image generation module 435 generates the long-scale image from the plurality of radiographic images with use of the CPU 401 and the GPU 406. The long-scale image is generated by positioning processing for defining a positional relationship among the plurality of radiographic images. The positioning processing includes rough adjustment processing for determining a rough layout among the images, and fine adjustment processing for adjusting the positions among the images with precision of several pixels, or precision of one pixel or less.

The rough adjustment processing is processing for determining which ends correspond to each other among the ends of the individual radiographic images with use of the information indicating the layout relationship among the plurality of radiographic imaging units 102a, 102b, and 102c. This processing is performed with use of the layout information acquired from the processing performed by the FPD layout acquisition module 431. The fine adjustment processing is performed by, for example, pattern matching processing with use of image information of a region overlapping among the plurality of radiographic images. This processing may be performed after the processing by the correction module 436.

The correction module 436 performs the processing for correcting an influence due to the characteristic of the sensor and the correction processing for reducing the number of structures appearing in the radiographic image(s) with use of the CPU 401 and the GPU 406. The processing for correcting the characteristic of the sensor includes, for example, the processing for correcting influences of the variation in the input/output characteristic of each of the pixels, the defective pixel, and the like, and this processing is performed with use of data such as data for the gain correction and a defective map that are acquired in advance. The correction processing for reducing the number of structures appearing in the radiographic image(s) is performed with use of the correction data for reducing the number of structures. This correction data is acquired by subtracting data acquired by carrying out the image-capturing with use of the same imaging system as the imaging system that captures this radiographic image and without the presence of the subject, after dividing this data by the data for the gain correction or dividing this data thereby after logarithmically converting this data. This correction data may be stored in each of the plurality of radiographic imaging units 102a, 102b, 102c in advance at the time of shipment from a factory or the like, or may be acquired before the long-scale imaging is carried out in each hospital.

In another exemplary embodiment, the function of the relay 103 is assumed to be provided to the control apparatus 104. In this case, the long-scale imaging system is configured in such a manner that, for example, the control apparatus 104 includes three second NICs 405b that communicate with the radiographic imaging units 102a, 102b, and 102c, and cables connected to the radiographic imaging units 102a, 102b, and 102c are directly connected to the control apparatus 104.

The display screen according to the present exemplary embodiment will be described with reference to FIG. 5. A display screen 500 includes an image area 501 where the radiographic image is displayed, a subject area 502 where information about the subject is displayed, a image-capturing information area 503 where the image-capturing information is displayed, an end button 504, and a state area 507 where information indicating the states of the plurality of radiographic imaging units 102a, 102b, and 102c is displayed. The example illustrated in FIG. 5 indicates the display screen after the long-scale imaging has been already carried out once when the long-scale imaging is supposed to be carried out a plurality of times. A long-scale image 508 is displayed in the image area 501. Information about a subject A is displayed in the subject area 502. Image-capturing information 505a about the image-capturing site that is the entire lower limb, and image-capturing information 505b about the image-capturing site that is the entire spine are displayed in the image-capturing information area 503 as image-capturing information 505. The information about the image-capturing site, and the number of radiographic imaging units 102 used or to be used for the long-scale imaging thereof are displayed side by side as the image-capturing information 505. The image-capturing information 505a is image-capturing information about the image-capturing that has been already carried out, and thumbnails of the radiographic images from the plurality of radiographic imaging units 102 are displayed therein while being arranged in a layout according to the layout relationship among the radiographic imaging units 102. In the example illustrated in FIG. 5, a thumbnail 506b of the radiographic image from the radiographic imaging unit 102b, a thumbnail 506c of the radiographic image from the radiographic imaging unit 102c, and a thumbnail 506a of the radiographic image from the radiographic imaging unit 102a are displayed while being arranged in this order. In this manner, the thumbnails are arranged based on the layout information, which allows the user to easily check whether the long-scale imaging has been appropriately carried out. On the other hand, if there is an error in the layout information, this results in a failure to arrange the thumbnails appropriately, which allows the user to be notified of whether the layout information is appropriate in an easily understandable manner.

On the other hand, the image-capturing information 505b is image-capturing information about the image-capturing that is not yet carried out, and a display indicating the layout relationship among the plurality of radiographic imaging units 102 is presented therein instead of the thumbnails. In the example illustrated in FIG. 5, a display ("FPD B") 507b corresponding to the radiographic imaging unit 102b, a display ("FPD C") 507c corresponding to the radiographic imaging unit 102c, and a display ("FPD A") 507a corresponding to the radiographic imaging unit 102a are displayed while being arranged so as to be located at display positions according to the layout relationship among the radiographic imaging units 102a, 102b, and 102c. This display allows the user to check whether the radiographic imaging units 102a, 102b, and 102c are appropriately laid out on the touch panel monitor 108 of the control apparatus 104 before the image-capturing. The control apparatus 104 may be configured to cause the states of the radiographic imaging units 102a, 102b, and 102c to be displayed by the displays 507a, 507b, and 507c at this time.

The information indicating the states of the plurality of radiographic imaging units 102 is displayed in the state area 507. The radiographic imaging units 102 for which the information indicating the states is displayed there may be the radiographic imaging units 102 corresponding to the currently specified image-capturing condition. If the image-capturing condition corresponding to the long-scale imaging is specified as illustrated in FIG. 5, the information indicating the states of the radiographic imaging units 102a, 102b, and 102c is displayed therein. In the state area 507, the pieces of information indicating the states of the plurality of radiographic imaging units 102 are displayed while being arranged on the display screen 500 at display positions according to the layout state among this plurality of radiographic imaging units 102. For example, if the radiographic imaging unit 102b and the radiographic imaging unit 102c are interchanged with the display screen displayed as illustrated in FIG. 5, this interchange results in a display of the respective states of the radiographic imaging units 102c, 102b, and 102a arranged in this order in the state area 507. Presenting the display in this manner allows the user to easily check the layout relationship among the plurality of radiographic imaging units 102.

The end button 504 is a button for ending an examination regarding the plurality of pieces of image-capturing information displayed on the display screen 500. If the end button 504 is pressed after an end of the image-capturing operations corresponding to all pieces of image-capturing information contained in this examination, this examination is ended. In this case, the CPU 401 generates the DICOM image file of the radiographic images regarding this examination, and causes the first NIC 405a to transmit this file to the PACS 154. On the other hand, if the end button 504 is pressed before the end of the image-capturing operations corresponding to the pieces of image-capturing information contained in this examination, this examination is set into a suspended state, and is stored into the storage unit 403 together with flag information indicating the suspended state.

The control apparatus 104 may be configured to cause the states of the individual radiographic imaging units 102 to be displayed in the displays 507a, 507b, and 507c, and cause readiness or unreadiness for the image-capturing to be clearly displayed in the state area 507 as a display indicating whether the long-scale imaging can be carried out. In this case, the state area 507 is displayed in such a manner that a color of the state area 507 is, for example, grayed if even any one of the plurality of radiographic imaging units 102 is in the first state, i.e., is not in the state prepared for the acquisition of the radiographic image. Further, for example, a text "NOT READY" is displayed in addition thereto. The prohibition of the long-scale imaging is clearly indicated by this display. On the other hand, if all of the plurality of radiographic imaging units 102 are in the second state prepared for the acquisition of the radiographic image, the color of the state region 507 is, for example, greened, and a text "READY" is displayed in addition thereto. The permission of the long-scale imaging is clearly indicated by this display. In this manner, the display of the touch panel monitor 108 is controlled according to whether any one of the plurality of radiographic imaging units 102 is in the first state or all of the plurality of radiographic imaging units 102 are in the second state, by which the readiness or the unreadiness for the image-capturing is clearly indicated.

Figure 6:
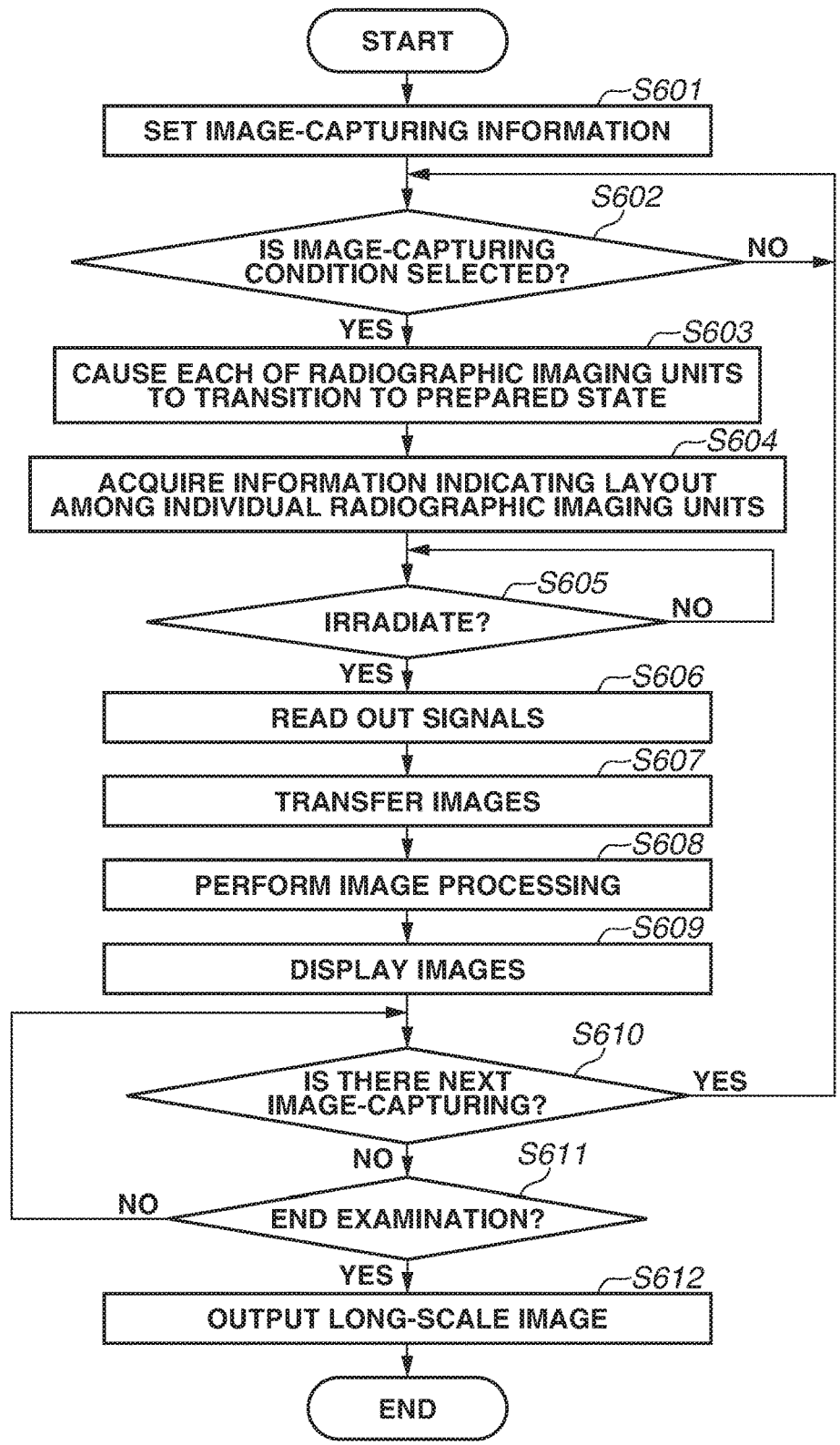
FIG. 6 is a flowchart illustrating a flow of processing regarding long-scale imaging according to the exemplary embodiment.

A flow of processing regarding the long-scale imaging according to the present exemplary embodiment will be described with reference to a flowchart illustrated in FIG. 6. A processing entity that performs the following processing is the CPU 401 of the control apparatus 104, unless otherwise noted specifically. The flow of the processing from steps S601 to S612 is controlled by the image-capturing control module 434.

In step S601, the CPU 401 sets one of pieces of image-capturing information (pieces of examination information) input from the RIS 151 as an examination target. In this process, for example, according to an operation input by which the user selects one of the plurality of pieces of examination information displayed in the form of a list, the CPU 401 sets this image-capturing information (the examination information) as the image-capturing target. At this time, for example, the CPU 401 executes the display control module 433 to cause the display screen 500 to be displayed on the display unit.

In step S602, the CPU 401 determines whether an operation input for selecting the image-capturing condition corresponding to the long-scale imaging that is contained in the image-capturing information (the examination information) is entered. At this time, if the image-capturing information (the examination information) contains a plurality of image-capturing conditions, information corresponding to the plurality of image-capturing conditions is displayed in the image-capturing information area 503 on the display screen 500, and the CPU 401 determines whether an operation input for selecting one of them is entered by the user. If the operation input for the selection is not entered (NO in step S602), the determination process in step S602 is repeated. If the operation input for the selection is entered (YES in step S602), the processing proceeds to a next process. The processing may be configured to automatically proceed to step S603 regardless of the process of step S602, if the image-capturing information (the examination information) contains only one image-capturing condition.

In step S603, the CPU 401 specifies the image-capturing condition corresponding to the long-scale imaging that has been selected by the operation input. Then, according to this specifying, the CPU 401 causes the second NIC 405b to transmit the signals for causing the states to transition to the prepared state to the plurality of radiographic imaging units 102a, 102b, and 102c involved in this long-scale imaging. In response thereto, each of the radiographic imaging units 102a, 102b, and 102c apply the bias voltage to the two-dimensional image sensor 120 by the main control circuit 150 controlling the bias power source 140, if the bias voltage is not applied to the two-dimensional image sensor 120. After that, each of the radiographic imaging units 102a, 102b, and 102c carries out the initialization of reading out the image signals from the pixel array by the driving circuit 130 to read out dark current signals stored in the pixels. After an end of the initialization, each of the radiographic imaging units 102a, 102b, and 102c transmits, to the control apparatus 104, the state information indicating that each of the plurality of radiographic imaging units 102a, 102b, and 102c is in the second state, which is the state prepared for the acquisition of the radiographic image, after the completion of the initialization.

In step S604, the CPU 401 acquires the layout information indicating the layout relationship among the plurality of radiographic imaging units 102a, 102b, and 102c to be used for the long-scale imaging. For example, in the case where the present processing is performed assuming that the long-scale imaging system is a system such as the system illustrated in FIG. 1, the CPU 401 acquires the information indicating the respective communication paths of the plurality of radiographic imaging units 102a, 102b, and 102c from the relay 103. The relay 103 includes a plurality of physical ports to which the cables 205a, 205b, and 205c from the platform connectors 206a, 206b, and 206c respectively provided to the housing portions 201a, 201b, and 201c are connected. This relay 103 identifies which physical port each of the signals from the radiographic imaging units 102a, 102b, and 102c is input from, thereby generating the correspondence relationships between the physical ports and the radiographic imaging units 102a, 102b, and 102c, i.e., the information indicating the respective communication paths of the radiographic imaging units 102a, 102b, and 102c. The CPU 401 of the control apparatus 104 receives this information from the second NIC 405b. The CPU 401 acquires the information indicating the layout relationship from the information indicating the communication paths acquired in this manner.

Figure 5:
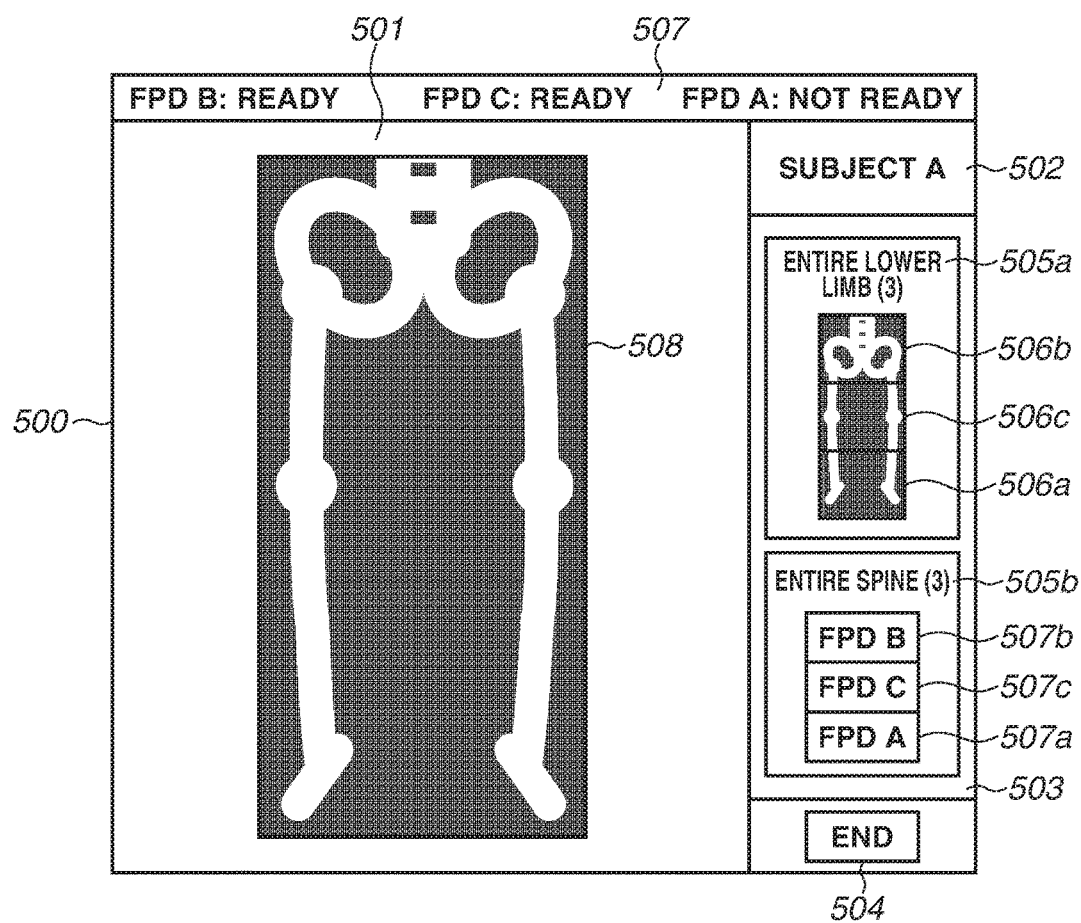
FIG. 5 illustrates an example of a display screen according to the exemplary embodiment.

As indicated by the image-capturing information 505b on the display screen 500 illustrated in FIG. 5, this information indicating the layout relationship is displayed as the information indicating the layout relationship among the plurality of radiographic imaging units 102a, 102b, and 102c to be used for the long-scale imaging corresponding to this image-capturing information 505b.

In step S605, the CPU 401 determines whether the irradiation switch is pressed. If the irradiation switch is pressed (YES in step S605), the processing proceeds to step S606.

Whether the irradiation switch should be pressed is determined, for example, with use of the display based on the states of the plurality of radiographic imaging units 102a, 102b, and 102c displayed on the display screen 500. More specifically, the display of the specific area on the display screen 500 is controlled according to whether any one of the plurality of radiographic imaging units 102a, 102b, and 102c is in the first state or all of the plurality of radiographic imaging units 102a, 102b, and 102c are in the second state based on the state information acquired from each of the plurality of radiographic imaging units 102a, 102b, and 102c. This is as described in the description of the display screen 500 illustrated in FIG. 5.

In step S606, the driving circuit 130 of each of the radiographic imaging units 102a, 102b, and 102c reads out the image signals acquired by detecting the radiation with which the subject is irradiated by the readout circuit 170 to generate the digital radiographic image.

In step S607, the wired communication circuit 180 or the wireless communication circuit 160 of each of the radiographic imaging units 102a, 102b, and 102c transmits the generated digital radiographic image to the control apparatus 104. Each of the plurality of radiographic imaging units 102a, 102b, and 102c transmits the preview image small in data quantity and then transmits the image that contains the remaining data after that, thereby completing the transmission of the radiographic image acquired from the image-capturing. At this time, in a case where each of the radiographic imaging units 102a, 102b, and 102c transmits the radiographic image via the wired communication circuit 180, each of the radiographic imaging units 102a, 102b, and 102c employs the communication method that sequentially transmits the preview image and the image containing the remaining data in response to the readout of the image signals. This transmission is carried out asynchronously with the other radiographic imaging units 102. On the other hand, in a case where each of the radiographic imaging units 102a, 102b, and 102c transmits the images via the wireless communication circuit 160, each of the radiographic imaging units 102a, 102b, and 102c restricts the transmission of the image that contains the remaining data until the completion of the transmission of the preview images from all of the radiographic imaging units 102a, 102b, and 102c, in consideration of such a problem that this image transmission may weigh on the communication capacity.

In step S608, the CPU 401 of the control apparatus 104 performs the image processing on the plurality of radiographic images acquired from the plurality of radiographic imaging units 102a, 102b, and 102c with use of the GPU 406 and the like. This processing is, for example, the processing for generating the long-scale image with use of the long-scale image generation module 435, and the processing for reducing the number of structure images with use of the correction module 436. In the process of step S608, first, the CPU 401 performs the processing for acquiring a preview long-scale image from the plurality of preview images, and then performs the processing for acquiring the long-scale image from the plurality of radiographic images larger in data amount than these preview images after that. This processing is performed with use of the layout information acquired in step S604. The processing for reducing the number of structure images is performed on the radiographic image specified based on the layout information with use of the correction data prepared for the processing for reducing the number of structure images that is specified based on the layout information.

In step S609, the CPU 401 causes the preview long-scale image and the long-scale image acquired from the processing performed by the GPU 406 and the like to be displayed on the display unit.

In step S610, the CPU 401 determines whether there is an image-capturing condition on which the image-capturing is not yet carried out. If there is such an image-capturing condition (YES in step S610), the processing proceeds to step S602. Then, the CPU 401 performs the long-scale imaging based on the new image-capturing condition. If there is no image-capturing condition on which the image-capturing is not yet carried out (NO in step S610), then in step S611, the CPU 401 determines whether to end the examination. If the CPU 401 does not end the examination (NO in step S611), the CPU 401 performs processing for waiting for an addition of an image-capturing condition on which the image-capturing is not yet carried out, or an instruction to end the examination. If the examination end button 504 is pressed at this time (YES in step S611), the CPU 401 ends the examination. In step S612, the CPU 401 causes the first NIC 405a to output the DICOM image file of the long-scale image to the PACS 155. With this output, the examination that contains the long-scale imaging is ended.

In the above-described example, the long-scale imaging system is assumed to carry out the long-scale imaging a plurality of times during a single examination. However, it is not limited thereto, and it may be assumed to carry out the long-scale imaging together with image-capturing using a different image-capturing method from the long-scale imaging during a single examination. In this manner, in the case of the imaging system capable of carrying out the long-scale imaging, when carrying out the long-scale imaging, the control apparatus 104 transmits the signals for causing the states of the plurality of radiographic imaging units 102a, 102b, and 102c to transition according to the specifying of the image-capturing condition. On the other hand, when carrying out the image-capturing using the single radiographic imaging unit 102, such as normal image-capturing, the control apparatus 104 transmits the signal for causing the state of this single radiographic imaging unit 102 to transition according to the specifying of the image-capturing condition. Further, when carrying out the long-scale imaging, the control apparatus 104 controls the display based on the state information acquired from each of the plurality of radiographic imaging units 102a, 102b, and 102c according to whether any one of the plurality of radiographic imaging units 102a, 102b, and 102c is in the first state or all of the plurality of radiographic imaging units 102a, 102b, and 102c are in the second state. When carrying out the image-capturing using the single radiographic imaging unit 102, the control apparatus 104 causes the information indicating the state of this single radiographic imaging unit 102 to be displayed.

Further, when carrying out the long-scale imaging, the control apparatus 104 acquires the layout information indicating the layout relationship among the plurality of radiographic imaging units 102a, 102b, and 102c. The radiographic image(s) acquired from at least one of the radiographic imaging unit(s) 102 specified based on this layout information is or are corrected based on the correction data specified based on the layout information.

Further, at the time executing the long-scale imaging, the control is performed so as to restrict the transmission of the image according to the communication of the other radiographic imaging units 102 in consideration of the problem that the image transmission may weigh on the communication capacity. On the other hand, at the time of the image-capturing using the single radiographic imaging unit 102, the image that contains the remaining data is transmitted according to the end of the transmission of the preview image because priority is placed on transmitting the image as quickly as possible in this case.

Processing for recognizing the positions where the radiographic imaging units 102a, 102b, and 102c are mounted, or processing for acquiring the layout information among them according to the exemplary embodiment will be described with reference to FIGS. 7 to 13.

Each of the wired communication circuit 180 and the wireless communication circuit 160 included in each of the radiographic imaging units 102a, 102b, and 102c has a unique identification number determined when being manufactured, and this number is called an address. Similarly, the control apparatus 104 also has a unique address. The communication therebetween is divided into data pieces, each of which is data small in size within a certain upper limit range that is called a packet (or a frame), and is transmitted and received packet by packet. The packet includes fields that hold an address of a transmission destination and an address of a transmission source, respectively. An apparatus at an end point or a relay point of the communication controls a path of the packet, receives the packet, and deletes an unnecessary packet by referring to values of these fields. In the present exemplary embodiment, Ethernet (registered trademark) is used as the communication path, and the identification number is referred to as the term "MAC address".

Figure 7:
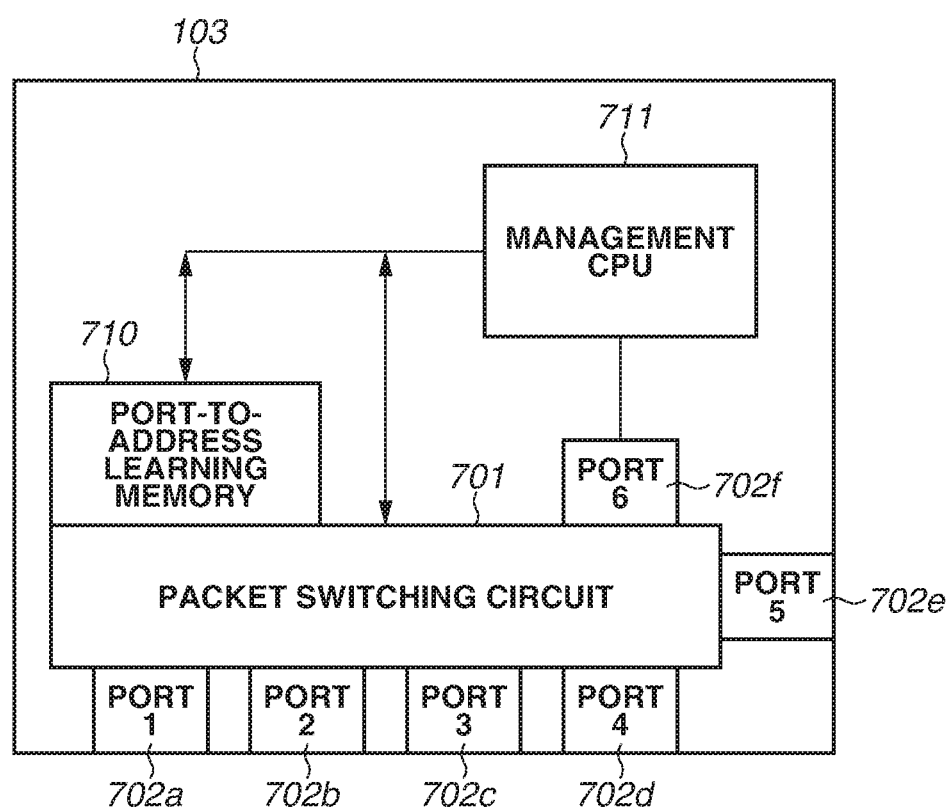
FIG. 7 illustrates a configuration of a relay according to the exemplary embodiment.

FIG. 7 illustrates an example of a configuration of the relay 103 built in the platform 101. The relay 103 serves as a network switch, and includes a plurality of ports 1 to 6 (ports 702a to 702f) to which the network cables 205 are connected. All of the ports 1 to 6 are connected to a built-in packet switching circuit 701. The packet switching circuit 701 operates so as to relay and output an input packet transmitted to a certain port to another port. At this time, the packet switching circuit 701 determines which port the packet should be relayed to or whether the packet should be relayed to all of the ports 1 to 6 by referring to the transmission destination field and the transmission source field of the packet. For this determination, the packet switching circuit 701 refers to not only the transmission destination field and the transmission source field of the input packet but also a content of a learning memory 710 included in the relay 103.

Figure 8:
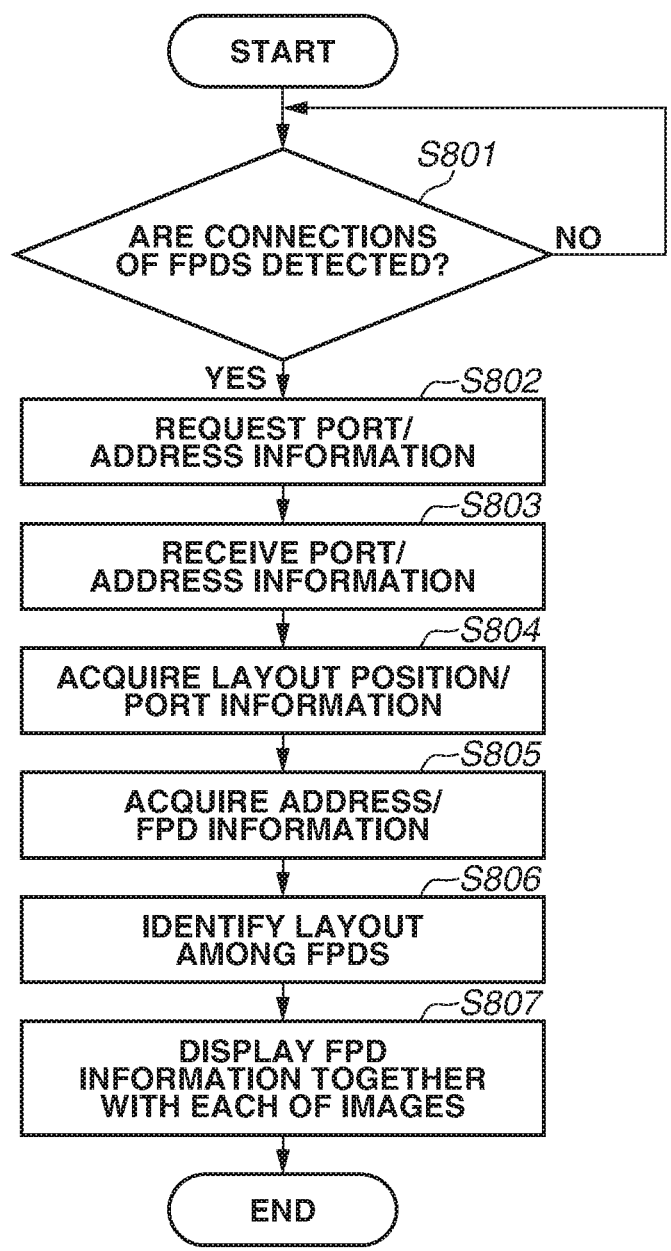
FIG. 8 is a flowchart illustrating a flow of processing for acquiring information indicating a layout relationship among a plurality of radiographic imaging units according to the exemplary embodiment.

A flow of the processing for acquiring the layout relationship according to one exemplary embodiment will be described with reference to a flowchart illustrated in FIG. 8. In step S801, the control apparatus 104 determines whether establishment of the connections of the radiographic imaging units 102a, 102b, and 102c to the control apparatus 104 is detected based on signals from the radiographic imaging units 102a, 102b, and 102c. The control apparatus 104 may be assumed to receive these signals via the relay 103. If the establishment of the connections is detected (YES in step S801), the processing proceeds to step S802.

In step S802, the CPU 401 of the control apparatus 104 causes the second NIC 405b to transmit a signal for requesting port/address information to the relay 103. The port/address information is information indicating the correspondence relationships between the physical ports of the relay 103 and the pieces of identification information of the radiographic imaging units 102a, 102b, and 102c respectively connected to these physical ports, such as the MAC addresses, and is an example of path information indicating the communication paths between the radiographic imaging units 102a, 102b, and 102c and the control apparatus 104. The identification information, such as the MAC address, is an example of information that is contained in information received by the relay 103 or the second NIC 405b and is used to identify each of the plurality of radiographic imaging units 102a, 102b, 102c that is the transmission source. Further, the information indicating the physical port is information used to identify a connection portion which the information received by the relay 103 or the second NIC 405b has passed through. This path information is generated by the relay 103. Processing for generating this path information will be described below with reference to FIG. 9 and drawings subsequent thereto.

In another exemplary embodiment, the control apparatus 104 is provided with NICs as many as the number of radiographic imaging units 102a, 102b, and 102c, and communicates with the radiographic imaging units 102a, 102b, and 102c via the plurality of NICs, without use of the relay 103. In this case, the control apparatus 104 acquires NIC/address information indicating correspondence relationships between the NICs and the pieces of identification information of the radiographic imaging units 102a, 102b, and 102c respectively connected to these NICs as the information indicating the communication paths between the radiographic imaging units 102a, 102b, and 102c and the control apparatus 104.

In step S803, the second NIC 405b receives the port/address information, which is an example of the path information, from the relay 103.

In another exemplary embodiment, the control apparatus 104 is provided with NICs as many as the number of radiographic imaging units 102a, 102b, and 102c, and communicates with the radiographic imaging units 102a, 102b, and 102c via this plurality of NICs, without use of the relay 103. In this case, the control apparatus 104 acquires NIC/address information indicating correspondence relationships between the NICs and the pieces of identification information of the radiographic imaging units 102a, 102b, and 102c respectively connected to these NICs as the information indicating the communication paths between the radiographic imaging units 102a, 102b, and 102c and the control apparatus 104. In this case, the processing performed in steps S802 and S803 are replaced with processing for acquiring the above-described path information.

In step S804, the CPU 401 acquires the correspondence information indicating the correspondence relationships between the communication paths and the radiographic imaging units 102a, 102b, and 102c. At this time, the CPU 401 acquires layout position/port information indicating the relationships between the physical ports and the layout positions of the radiographic imaging units 102a, 102b, and 102c that communicate via these physical ports, as an example of the correspondence information. The following information is acquired as the information indicating the layout positions of the radiographic imaging units 102a, 102b, and 102c. In a case where the plurality of radiographic imaging units 102a, 102b, and 102c is vertically lined up as illustrated in FIG. 1, the radiographic imaging units 102a, 102b, and 102c are assumed to be associated with numbers 101, 201, and 301 in the order from the top. In a case where the physical ports and the layout positions correspond to each other in the fixed relationships as described above, the control apparatus 104 stores, in the storage unit 403 in advance, information indicating an association between the layout position information and the port information, like information indicating that the physical port 1 and the layout position 101 are associated with each other, the physical port 2 and the layout position 201 are associated with each other, and the physical port 3 and the layout position 301 are associated with each other. Then, the CPU 401 reads out this information, thereby acquiring the layout position/port information.

In a case where the physical ports and the layout positions do not correspond to each other in the fixed relationships, the CPU 401 may be assumed to acquire this correspondence information according to, for example, an operation input entered by the user.

In step S805, the CPU 401 acquires address/FPD information. The address/FPD information is information indicating correspondence relationships between the MAC addresses, which are the pieces of address information of the radiographic imaging units 102a, 102b, and 102c, and the names of the radiographic imaging units (FPDs) 102a, 102b, and 102c. These names of the radiographic imaging units 102a, 102b, and 102c are used as information indicating the radiographic imaging units 102a, 102b, and 102c on the display screen 500.

In step S806, the CPU 401 identifies the layout among the radiographic imaging units (FPDs) 102a, 102b, and 102c with use of the above-described path information, correspondence information, and address/FPD information by executing a layout information acquisition module 431. For example, in a case where there are the FPD A, the FPD B, and the FPD C as the radiographic imaging units 102, the reference to the above-described information results in the layout identified as the radiographic imaging units 102 being arranged in an order of, for example, the FPD B, the FPD C, and the FPD A.

In step S807, the CPU 401 causes the radiographic images from the plurality of radiographic imaging units 102a, 102b, and 102c to be displayed with information regarding the layout among the radiographic imaging units 102a, 102b, and 102c added thereto based on the pieces of identification information and the names of the radiographic imaging units 102a, 102b, and 102c associated with these images, when causing these images to be displayed. Alternatively, the control apparatus 104 may be configured to cause the plurality of radiographic images to be displayed while being arranged according to the information regarding this layout.

Alternatively, the control apparatus 104 may be configured to arrange information indicating each of the plurality of radiographic imaging units 102a, 102b, and 102c according to the above-described layout information instead of the process of step S807, if the control apparatus 104 has not received the radiographic images yet. This processing can realize the display of the state area 507 and the displays of the displays 507a, 507b, and 507c illustrated in FIG. 5, thereby allowing the user to be notified of the layout relationship among the radiographic imaging units 102a, 102b, and 102c before carrying out the image-capturing.

Figure 9:
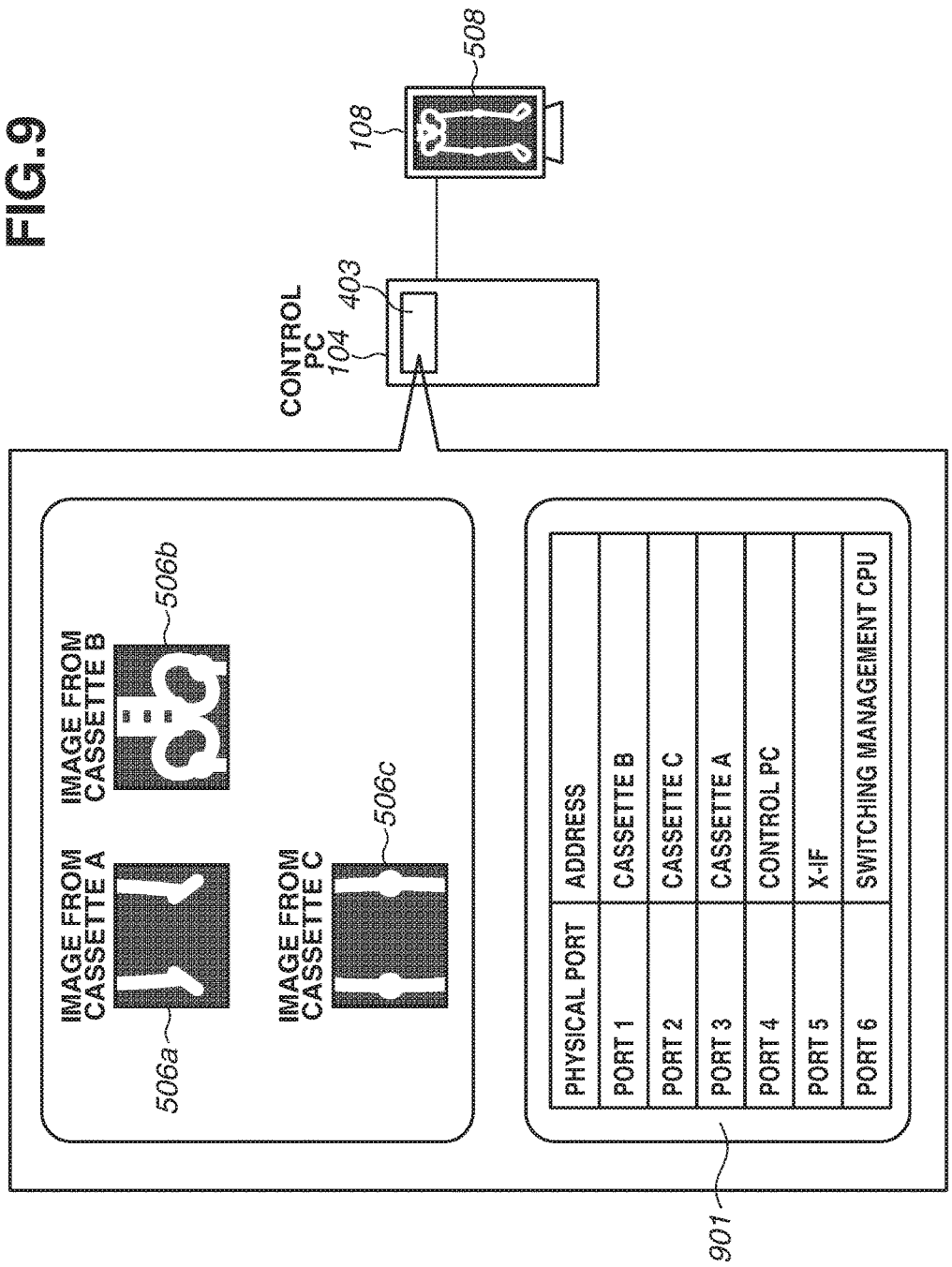
FIG. 9 illustrates an overview of processing for generating a long-scale image.

FIG. 9 illustrates how the control apparatus 104 connectively combines the images received from the individual radiographic imaging units 102a, 102b, and 102c during the long-scale imaging. The radiographic image received from each of the radiographic imaging units 102a, 102b, and 102c contains the radiographic image of each portion of the subject, and the information for identifying the radiographic imaging unit 102a, 102b, or 102c, which is the source that has transmitted this image. On the other hand, separately from these radiographic images, the control apparatus 104 has the path information indicating the communication paths, which is the information indicating the connections of the individual cassettes A, B, and C to the respective ports that the control apparatus 104 has received by inquiring to the relay 103. Use of them in combination allows the control apparatus 104 to determine how the individual images should be connected to one another in terms of the order among these images. The control apparatus 104 performs the image processing based on this determination, and provides the long-scale image to the touch panel monitor 108.

An operation algorithm of the relay 103 will be described. The learning memory 710 stores relationships between the physical ports 1 to 6 and the addresses of the apparatuses connected to the physical ports 1 to 6. When the operation starts, the content of this memory 710 is empty, and the relay 103 is placed into a state of "having no knowledge about the relationships between the ports 1 to 6 and the addresses of the apparatuses connected to the ports 1 to 6". The packet switching circuit 701 operates to output the input packet to another port, and therefore determines a port to which the input packet should be output by checking the transmission destination field of the input packet at this time. The packet switching circuit 701 collates an address value in the transmission destination field of the input packet to determine whether a value corresponding thereto is stored in the leaning memory 710. If this address value is contained in the memory 710, the packet switching circuit 701 outputs the packet to the port corresponding to this address value. Otherwise, the packet switching circuit 701 outputs the packet to all of the ports 1 to 6 in parallel because not knowing which port is connected to the apparatus corresponding to the transmission destination at this moment. On the other hand, while engaging this relay operation, because being able to figure out that the apparatus having this address value is connected to the port where this packet has reached by referring to the transmission source field of the input packet, the packet switching circuit 701 stores this relationship into the learning memory 710 to learn it. After that, the packet switching circuit 701 repeats this operation.

Figure 10:
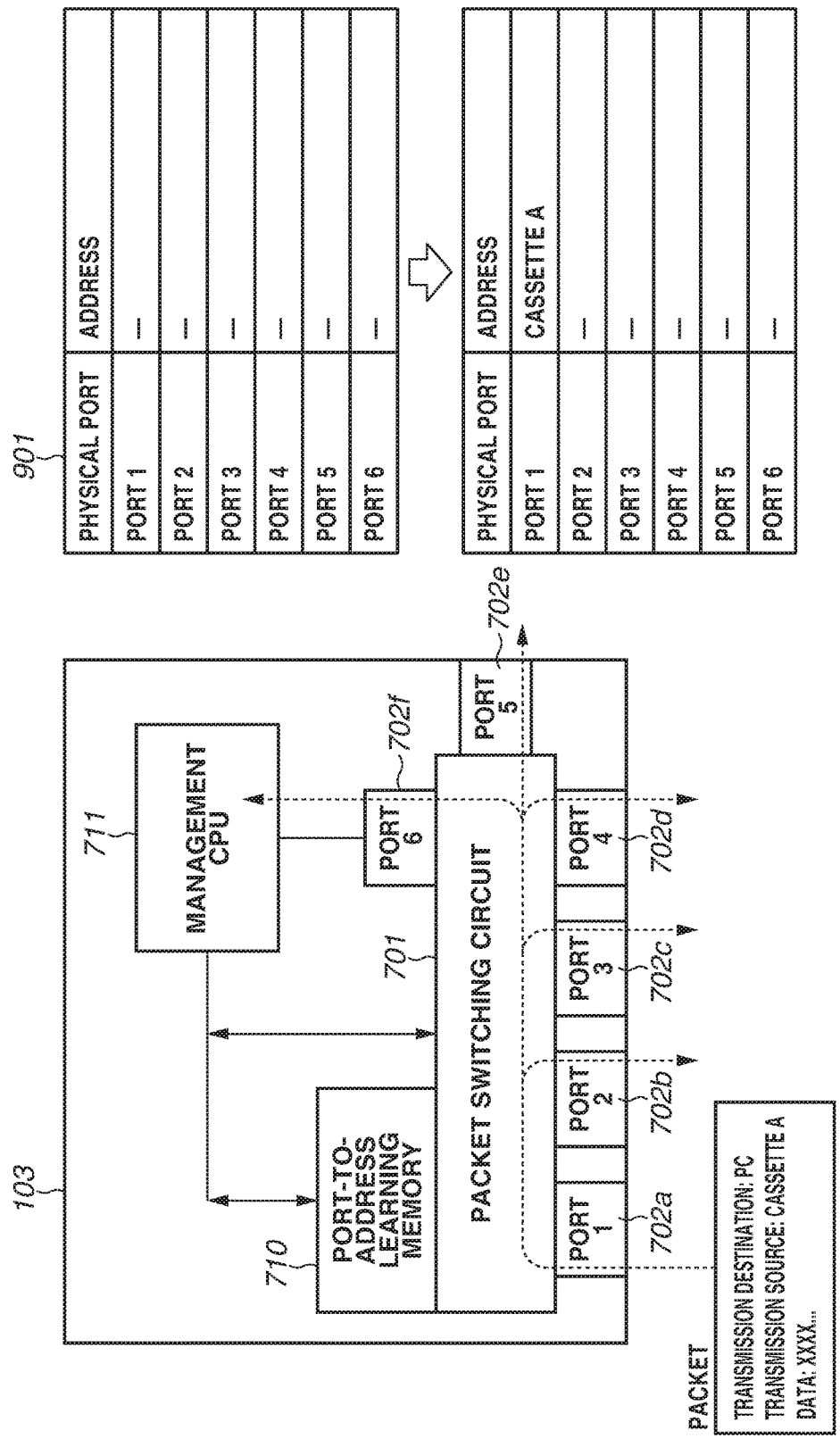
FIG. 10 illustrates an overview of processing for acquiring information indicating communication paths by the relay.

FIG. 10 illustrates how the relay 103 in an initial state receives a first packet and starts the leaning. In the initial state, the content of the learning memory 710 is empty as indicated by an upper right table illustrated in FIG. 10. FIG. 10 illustrates the relay 103 with a packet arrived in this state, specifying the control apparatus 104 as the transmission destination and indicating the cassette A (the radiographic imaging unit 102a) as the transmission source. Because no address corresponding to this transmission destination is stored in the learning memory 710, the input packet is relayed so as to be distributed to all of the ports 1 to 6 as indicated by dotted arrows. On the other hand, the address of the cassette A (the radiographic imaging unit 102a) is written in the transmission source field of the input packet, which reveals that the cassette A is connected to the port 1. To learn that, the packet switching circuit 701 stores the address of the "cassette A (the radiographic imaging unit 102a" into a field of the port 1 in the learning memory 710. As a result, a memory of one entry is stored in the learning memory 710 as a result of the learning, as indicated by a lower right table illustrated in FIG. 10.

Figure 11:
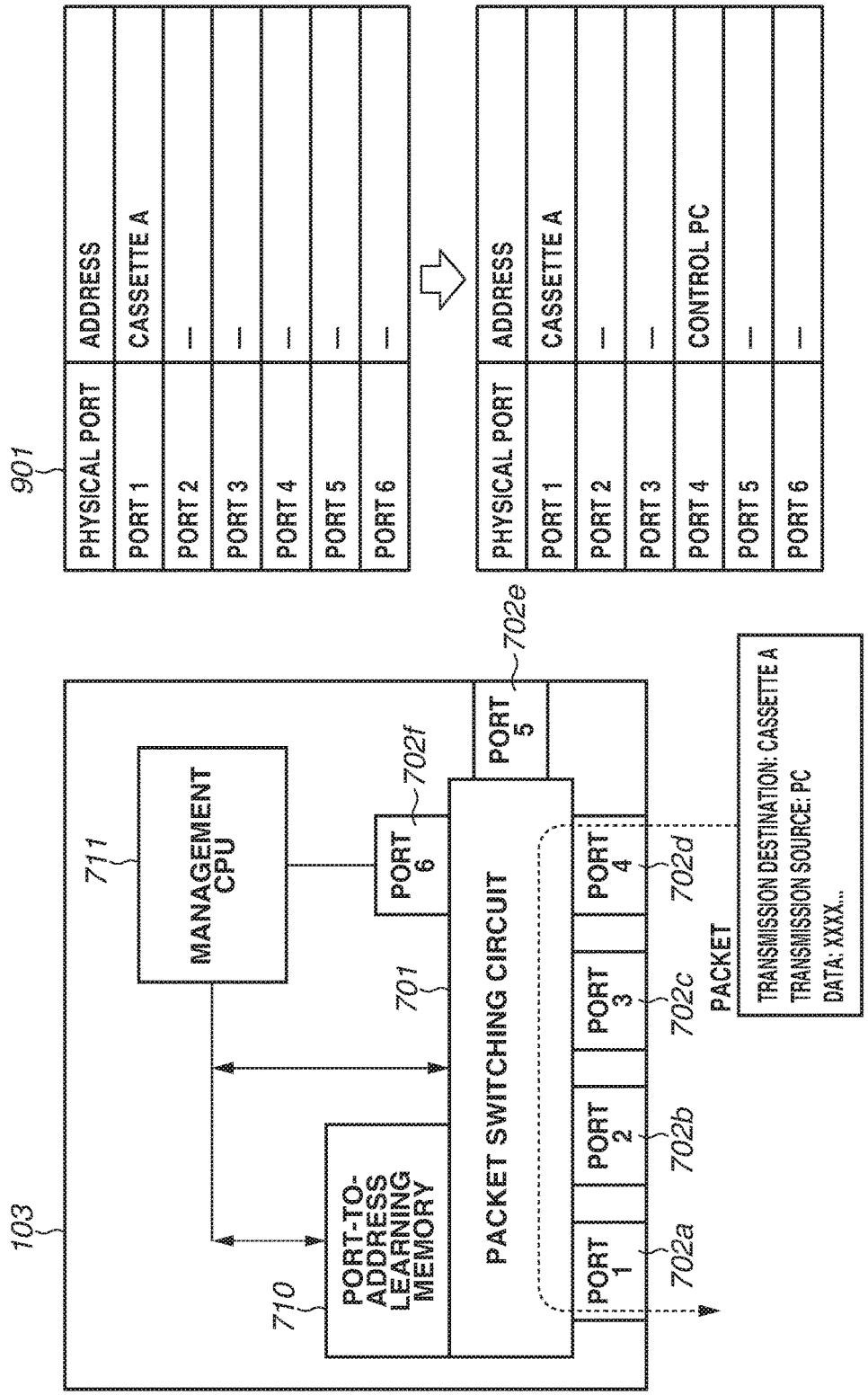
FIG. 11 illustrates the overview of the processing for acquiring the information indicating the communication paths by the relay.

FIG. 11 illustrates how the relay 103 operates when a packet as a response is transmitted from the control apparatus (a control PC) 104 to the port 4 after the operation illustrated in FIG. 10. The packet as the response contains a reverse transmission destination and a reverse transmission source of the packet illustrated in FIG. 10, and specifies the cassette A (the radiographic imaging unit 102a) as the transmission destination and indicates the control apparatus (the control PC) 104 as the transmission source. When collating the cassette A, which is the address of the transmission destination, within the learning memory 710, the packet switching circuit 701 can find out that the "cassette A (the radiographic imaging unit 102a)" is connected to the port 1 due to the result learned earlier and stored therein. Therefore, the packet switching circuit 701 relays this packet only to the port 1 without distributing the packet. On the other hand, the address of the control apparatus (the control PC) 104 is written as the address of the transmission source, which reveals that the control apparatus 104 is connected to the port 4. This is learned in a similar manner to the above-described operation, and is stored into the learning memory 710.

Through this operation, the network switch operates so as to prevent an unnecessary packet from multiplying in the network.

Figure 12:
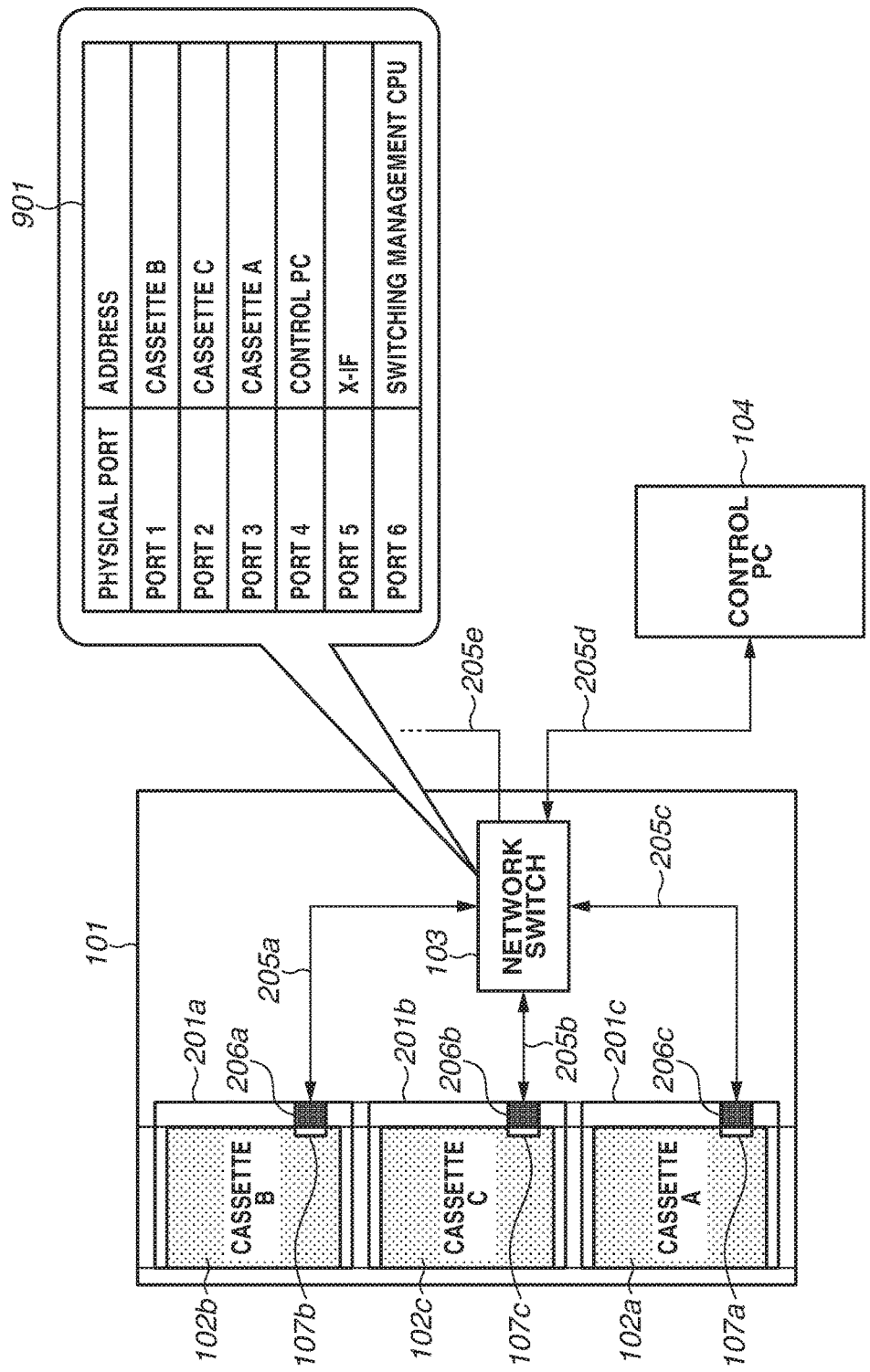
FIG. 12 illustrates an example of the information indicating the communication paths.

FIG. 12 illustrates the platform 101 with the plurality of cassettes A, B, and C mounted thereon, and the relay 103 having completed the leaning processing by performing the communication between the cassettes A, B, and C, and the control apparatus 104. The platform connectors 206a, 206b, and 206c, and the physical ports of the relay 103 correspond to each other in the fixed relationships as described above, and therefore the completion of the learning about the correspondence relationships between the physical ports and the MAC addresses of the cassettes A, B, and C is equivalent to that the arrangement order in which the cassettes A, B, and C are mounted on the platform 101 has been figured out. Actually, the control apparatus 104, which has received the information indicating these communication paths, acquires the information indicating the layout relationship among the plurality of radiographic imaging units 102a, 102b, and 102c, and identifies the respective layout positions of the plurality of radiographic imaging units 102a, 102b, and 102c.

In the example illustrated in FIGS. 10 and 11, the learning about the addresses has been described assuming that the communication starts from each of the plurality of radiographic imaging units 102a, 102b, 102c side when the learning about the addresses starts, but is not limited thereto. First communication may start from the control apparatus 104 side. Further, the learning about the addresses has been described assuming that this learning proceeds based on the packet clearly specifying the transmission destination, but is not limited thereto. For example, the learning about the addresses may be such an operation that the communication starts with a packet specifying all transmission destinations (a broadcast packet).

In the exemplary embodiment, the relay 103 includes a management CPU 711, and can monitor and change states of the packet switching circuit 701 and the learning memory 710. The management CPU 711 can also participate in communication in the network because the management CPU 711 is connected to an internal port (the port 6) of the packet switching circuit 701. The management CPU 711 can also transmit a reply reporting the states of the packet switching circuit 701 and the learning memory 710 in response to communication of an inquiry from outside via the network.

Figure 13:
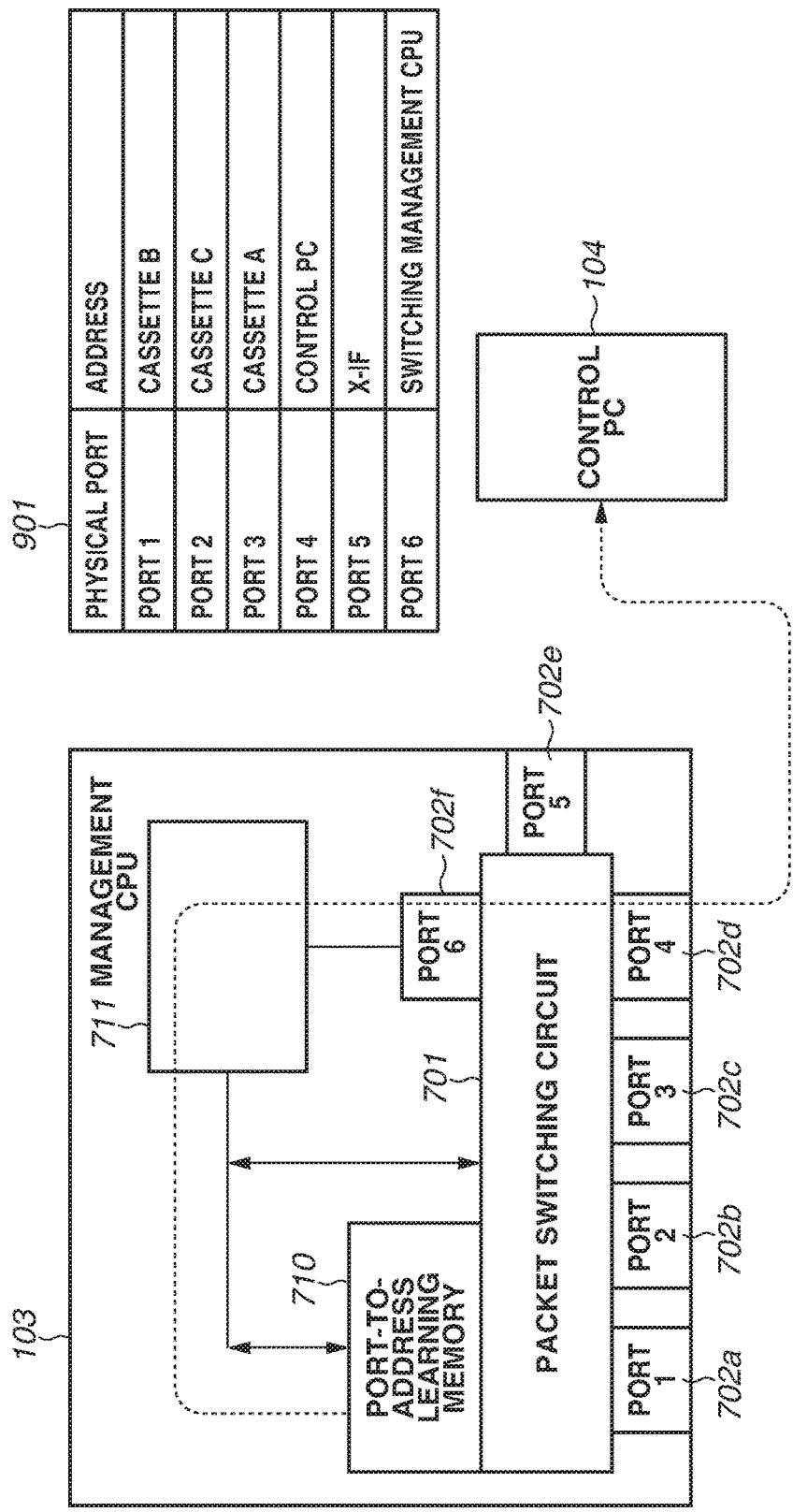
FIG. 13 illustrates an overview of processing for transmitting the information indicating the communication paths to the control apparatus.

FIG. 13 illustrates how the management CPU 711 transmits a reply notifying the control apparatus 104 of the content of the learning memory 710 in response to an inquiry from the control apparatus 104. The control apparatus 104 can recognize the position on the platform 101 where each of the radiographic imaging units 102*a*, 102*b*, and 102*c* is mounted by referring to a content of this reply.

A characteristic required for the relay 103 according to the present exemplary embodiment is different compared to general-use network switches, as will be described below.

The general network switches include a learning table configured so as to permit a plurality of MAC addresses to be associated with one port. Further, a MAC address registered in the learning table for once is subjected to deletion of a result of the learning if a packet having this address value does not reach this port for a predetermined time period. These characteristics are required because the general network switches are intended to be used in a cascade connection. More specifically, it is considered that a port connecting one switch to another switch leads to a plurality of communication end points further beyond the other switch under such a situation that a plurality of network switches is connected in a cascade manner. Therefore, the learning table should be configured to permit a plurality of MAC addresses to be associated with one port. Further, the switches can detect a physical signal disconnection at their own ports, but are not equipped with measures for detecting whether communication further beyond an adjacent switch remains with respect to the port connecting switches. Therefore, it is difficult to detect when to delete a result of learning a specific MAC address, which necessitates employment of a method that manages the deletion based on time.

In comparison thereto, the relay 103 according to the present exemplary embodiment does not have to consider the cascade connection with respect to the ports 1 to 3 to which the cassettes A, B, and C are intended to be connected. Further, it can be assumed that the same cassette is continuously kept connected to the port unless the physical signal disconnection occurs. Therefore, only one MAC address is enough as a MAC address permitted to be associated with one port. Further, the result of the learning does not have to be deleted according to the time-based management unless the physical signal disconnection occurs. It is rather desirable to refrain from deleting the result of the learning according to the time-based management in consideration of such a risk that deleting the result of the learning obscures the arrangement order in which the cassettes A, B, and C are mounted.

In view of this characteristic, the relay 103 according to the exemplary embodiment does not delete the result of the learning according to an elapse of time but deletes the result of the learning when the physical signal disconnection occurs with respect to at least a part of the ports 1 to 6. The term "physical signal disconnection" refers to, for example, becoming unable to confirm whether a link is established by an exchange of an idle pattern in Ethernet (registered trademark).

In the above description, the communication paths and the relay 103 have been described assuming that Ethernet (registered trademark) and the layer 2 network switch are used as them, but are not limited thereto and may be realized by another technique and layer. Further, in the exemplary embodiment, the network switch is installed in the holder, but is not limited thereto and may be built in, for example, the control apparatus (the control PC) 104. Further, the relay 103 is not limited to being implemented as hardware, and the operation thereof may be realized as software.

Figure 14:
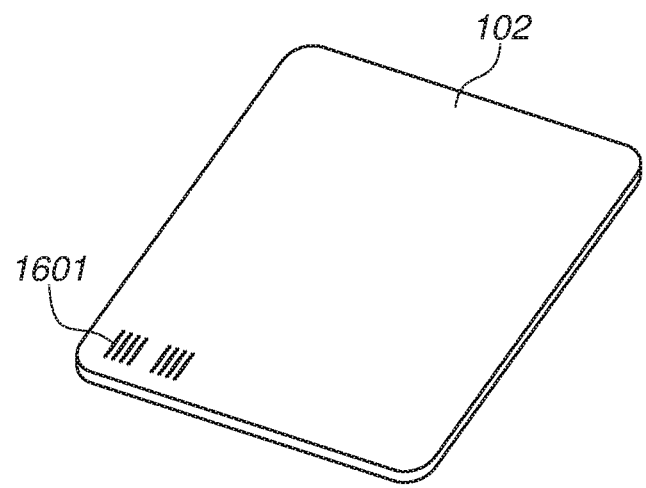
FIG. 14 illustrates a configuration of a radiographic imaging unit according to another exemplary embodiment.
Figure 15:
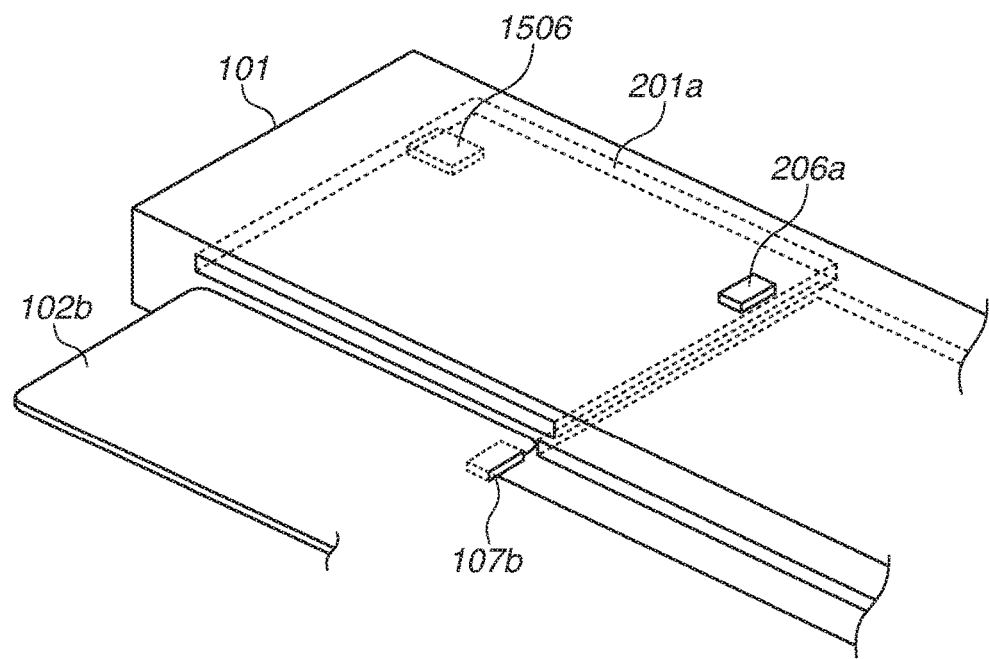
FIG. 15 illustrates a configuration of a platform according to the other exemplary embodiment.

Processing for acquiring the layout information according to another exemplary embodiment will be described with reference to FIGS. 14 and 15. The long-scale imaging platform 101 has the three positions where the radiographic imaging units 102*a*, 102*b*, and 102*c* are fixed, and includes a barcode reader 1506 (illustrated in FIG. 15), which is an example of a detection unit configured to detect the identification information, at each of the fixation positions. On the other hand, the radiographic imaging unit 102 includes a barcode 1601 printed on a back surface thereof as illustrated in FIG. 14. The position of each of the units is determined in such a manner that the barcode 1601 passes through a position where the barcode reader 1506 is supposed to read the barcode 1601 during the course of mounting the radiographic imaging unit 102 at each of the fixation positions of the platform 101 (FIG. 15).

The barcode 1601 is provided with a different code for each of the radiographic imaging units 102*a*, 102*b*, and 102*c*, and is configured to allow the individual unit to be identified. A signal line of each of the barcode readers 1506 in the long-scale imaging platform 101 is extended out of the platform 101 so as to be connectable to the control apparatus 104. When passing through the position where the barcode reader 1506 is supposed to read the barcode 1601, the barcode 1601 is read and individual identification information is transmitted to the control apparatus 104.

The control apparatus 104 can recognize at which position each of the radiographic imaging units 102*a*, 102*b*, and 102*c* is fixed in the platform 101 by determining from which barcode reader 1506 each of the pieces of individual identification information is transmitted. A result of the recognition is displayed on the touch panel monitor 108 connected to the control apparatus 104.

Further, whether the barcode 1601 can be successfully read is displayed on a not-illustrated indicator provided at the platform 101, so that the user can check whether the barcode 1601 can be successfully recognized without moving to the front of the touch panel monitor 108.

When the user completes the operation of mounting the radiographic imaging units 102*a*, 102*b*, and 102*c* onto the platform 101, and the software can confirm that the radiographic imaging units 102*a*, 102*b*, and 102*c* are mounted normally, the software displays the completion of the preparation on the touch panel monitor 108 connected to the control apparatus 104. The user confirms the display indicating the completion of the preparation, and carries out the image-capturing. As illustrated in FIG. 1, the image-capturing is carried out in such a manner that the subject is positioned in front of the platform 101, and the subject in the wide range extending across the plurality of radiographic imaging units 102*a*, 102*b*, and 102*c* can be imaged by being irradiated with the radiation a single time.

At this time, the radiographic imaging units 102*a*, 102*b*, and 102*c* transmit the radiographic images to the control apparatus 104, for example, wirelessly. Then, in a case where the radiographic imaging units 102*a*, 102*b*, and 102*c* are CR cassettes, the user dismounts the cassettes A, B, and C and sets the cassettes A, B, and C on a reader after carrying out the image-capturing. The reader reads out latent images from the imaging plates, and transmits the images to the control apparatus 104. At the same time as that, the reader reads the barcodes 1601 printed on the back surfaces of the radiographic imaging units 102*a*, 102*b*, and 102*c*, and transmits the images and the pieces of individual identification information in combination. Therefore, the control apparatus 104 can determine which cassette has captured which image.

In the above-described example, each of the barcode readers 1506 is connected to the control apparatus 104 by being individually separately wired, but is not limited thereto and may be connected by any communication method that can associate the positions where the cassettes A, B, and C are mounted with the contents of the barcodes 1601. For example, the long-scale imaging system may be configured in such a manner that the relay 103 is provided within the platform 101, and the relay 103 generates a communication telegram, in which an ID of the barcode reader 1506 and the content of the barcode 1601 are combined to each other, to then transmit the communication telegram to an image processing PC via a single signal line. Further, the control apparatus 104 and the touch panel monitor 108 with which the user confirms the completion of the preparation, and the apparatus that displays the result of the image processing may be different apparatuses from each other.

Further, in the above-described example, the barcodes 1601 are each read upon an insertion operation, but are not limited thereto and may be read in a static state after being inserted. Further, the display of the individual identification information has been described assuming that the barcodes 1601 are each used as this display by way of example, but is not limited thereto. The individual identification information may be displayed with use of an element that actively emits light, or may be displayed over time. For example, the identification code may be displayed with use of a liquid crystal display device that can present a matrix display, or light indicating the identification code may be emitted as a serial signal by an infrared light-emitting element.

According to the above-described exemplary embodiment, the use of the information indicating the communication paths of the radiographic imaging units 102a, 102b, and 102c allows the layout among the radiographic imaging units 102a, 102b, and 102c to be easily identified. Further, this method eliminates the necessity of using the radiographic images to identify the layout, and for example, allows the layout among the radiographic imaging units 102a, 102b, and 102c to be acquired even before the image-capturing is carried out. In this case, the user can reduce mistakes in work of making preparations for the image-capturing in advance.

Further, according to the above-described exemplary embodiment, the detection units read the pieces of identification information of the radiographic imaging units 102a, 102b, and 102c, which allows the layout among the radiographic imaging units 102a, 102b, and 102c to be easily identified. Further, this method eliminates the necessity of using the radiographic images to identify the layout, and for example, allows the layout among the radiographic imaging units 102a, 102b, and 102c to be acquired even before the image-capturing is carried out. In this case, the user can reduce mistakes in the work of making preparations for the image-capturing in advance.

The control apparatus 104 in the above-described exemplary embodiments is a single apparatus. However, in another exemplary embodiment, the functions of this image-capturing control apparatus 104 are realized by a control system including a plurality of information processing apparatuses. In this case, the plurality of information processing apparatuses each includes a communication circuit, and is communicable with one another by using this communication circuit. One of the plurality of information processing apparatuses can be configured to function as an image processing unit that generates the long-scale image, and another apparatus can be configured to function as a control unit. This plurality of information processing apparatuses only has to be communicable at a predetermined communication rate, and does not have to be set up in a same hospital facility or a same country. Further, this control system can also be configured to use, for example, a server apparatus or a server group shared among a plurality of control systems as the image processing unit.

Further, exemplary embodiments of the present invention also include an exemplary embodiment in which a program of software capable of realizing the functions of the above-described exemplary embodiments is supplied to a system or an apparatus, and a computer of this system or apparatus reads out and executes a code of the supplied program.

Therefore, the program code itself installed in this computer for realizing the processing according to the exemplary embodiments by the computer is also one exemplary embodiment of the present invention. Further, an operating system (OS) or the like running on the computer partially or entirely performs the actual processing based on an instruction contained in the program read out by the computer, and the functions of the above-described exemplary embodiments can also be realized by this processing.

An exemplary embodiment constructed by arbitrarily combining the above-described exemplary embodiments is also included in exemplary embodiments of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-017886, filed Jan. 30, 2015, and No. 2015-017889, filed Jan. 30, 2015, which are hereby incorporated by reference herein in their entirety.

The invention claimed is:

1. A radiographing system comprising:
a plurality of radiographic imaging units configured to acquire a plurality of radiographic images;
a communication unit to which the plurality of radiographic imaging units is connected; and
a storage medium storing instructions and a processor executing the instructions to function as:
an acquisition unit configured to acquire path information indicating a communication path between each of the plurality of radiographic imaging units connected to the communication unit and the communication unit, and
an output unit configured to output an image acquired from the plurality of radiographic images based on the path information.

2. The radiographing system according to claim 1, wherein the processor executes the instructions to further function as a reception unit configured to receive information from each of the plurality of radiographic imaging units, wherein the communication unit includes a plurality of connection portions connected to the plurality of radiographic imaging units in a wired manner, and wherein the acquisition unit acquires the path information based on information for identifying one of the plurality of radiographic imaging units that is a transmission source, which is contained in the information received by the reception unit, and information for identifying a connection portion through which the received information has passed.

3. The radiographing system according to claim 1, wherein the acquisition unit acquires correspondence information indicating correspondence relationships between the communication paths from the plurality of radiographic imaging units to the communication unit, and layout positions of the plurality of radiographic imaging units, and
wherein the output unit outputs the image acquired from the plurality of radiographic images based on the path information and the correspondence information.

4. The radiographing system according to claim 3, wherein the processor executes the instructions to further function as a generation unit configured to generate a long-scale image acquired by splicing the plurality of radiographic images based on the correspondence information and the path information, and
  wherein the output unit causes the long-scale image to be displayed on a display unit.

5. The radiographing system according to claim 3, wherein the processor executes the instructions to further function as an image processing unit configured to perform image processing on at least one of the plurality of radiographic images based on the correspondence information and the path information.

6. The radiographing system according to claim 1, wherein the processor executes the instructions to further function as a detection unit configured to detect establishment of wired connections of the plurality of radiographic imaging units to the communication unit,
  wherein the acquisition unit acquires the path information indicating the communication paths between the plurality of radiographic imaging units and the communication unit according to the detection of the establishment of the wired connections by the detection unit.

7. The radiographing system according to claim 1, wherein the output unit causes a plurality of images corresponding to the plurality of radiographic images to be displayed in an arranged manner on a display unit.

8. The radiographing system according to claim 1, wherein the output unit outputs the image acquired from the plurality of radiographic images outside.

9. The radiographing system according to claim 7, wherein the output unit further controls display positions of displays indicating the plurality of radiographic imaging units on the display unit based on the correspondence information and the path information.

10. The radiographing system according to claim 1, further comprising:
  a platform including a plurality of housing portions configured to house the plurality of radiographic imaging units; and
  connection portions respectively provided to the plurality of housing portions and configured to connect the plurality of radiographic imaging units and the communication unit to each other,
  wherein the output unit outputs the image acquired from the plurality of radiographic images according to a layout among the plurality of housing portions.

11. A control apparatus comprising:
a relay;
a communication circuit configured to communicate with the relay connected to, in a wired manner, a plurality of radiographic imaging units, and configured to acquire a plurality of radiographic images; and
a storage medium storing instructions and a processor executing the instructions to function as:
  an acquisition unit configured to acquire path information indicating a communication path between each of the plurality of radiographic imaging units connected to the communication unit and the communication unit, and
  an output unit configured to output an image acquired from the plurality of radiographic images based on the path information.

12. A control apparatus comprising:
a communication unit including a plurality of connection portions to which a plurality of radiographic imaging units configured to acquire a plurality of radiographic images is connected in a wired manner; and
a storage medium storing instructions and a processor executing the instructions to function as:
  an acquisition unit configured to acquire path information indicating a communication path between each of the plurality of radiographic imaging units connected to the communication unit and the communication unit, and
  an output unit configured to output an image acquired from the plurality of radiographic images based on the path information.

13. A radiographing system comprising:
a plurality of radiographic imaging units configured to acquire a plurality of radiographic images;
a communication unit to which the plurality of radiographic imaging units is connected in a wired manner;
a memory configured to store correspondence information indicating correspondence relationships between communication paths from the plurality of radiographic imaging units to the communication unit, and layout positions of the plurality of radiographic imaging units; and
a storage medium storing instructions and a processor executing the instructions to function as:
  an acquisition unit configured to acquire path information indicating the communication path between each of the plurality of radiographic imaging units connected to the communication unit and the communication unit, and
  a display control unit configured to control display positions of displays indicating the plurality of radiographic imaging units on a display unit based on the correspondence information and the path information.

14. A control apparatus comprising:
a relay;
a communication circuit configured to communicate with the relay connected to, in a wired manner, a plurality of radiographic imaging units, and configured to acquire a plurality of radiographic images; and
a storage medium storing instructions and a processor executing the instructions to function as:
  an acquisition unit configured to acquire path information indicating a communication path between each of the plurality of radiographic imaging units connected to the communication circuit and the communication circuit, and
  a display control unit configured to control display positions of displays indicating the plurality of radiographic imaging units on a display unit based on the path information.

15. A control apparatus comprising:
a communication unit including a plurality of connection portions to which a plurality of radiographic imaging units configured to acquire a plurality of radiographic images is connected in a wired manner; and
a storage medium storing instructions and a processor executing the instructions to function as:
an acquisition unit configured to acquire path information indicating a communication path between each of the plurality of radiographic imaging units connected to the communication unit and the communication unit, and
a display control unit configured to control display positions of displays indicating the plurality of radiographic imaging units on a display unit based on the path information.

16. A control method for controlling a radiographing system including a communication unit connected to a plurality of radiographic imaging units configured to acquire a plurality of radiographic images, the control method comprising:
acquiring correspondence information indicating correspondence relationships between communication paths from the plurality of radiographic imaging units to the communication unit, and layout positions of the plurality of radiographic imaging units;
acquiring path information indicating the communication path between each of the plurality of radiographic imaging units connected to the communication unit and the communication unit; and
outputting an image acquired from the plurality of radiographic images based on the path information.

17. A control method for controlling a radiographing system including a communication unit connected to a plurality of radiographic imaging units configured to acquire a plurality of radiographic images, the control method comprising:
acquiring path information indicating a communication path between each of the plurality of radiographic imaging units connected to the communication unit and the communication unit; and
controlling display positions of displays indicating the plurality of radiographic imaging units on a display unit based on the path information.

18. A non-transitory computer-readable storage medium storing a program for causing a computer to perform the control method according to claim 16.

19. A radiographing system comprising:
a plurality of radiographic imaging units;
a platform including a plurality of housing portions configured to house the plurality of radiographic imaging units;
a plurality of detection units respectively provided to the plurality of housing portions and configured to detect a plurality of pieces of identification information of the plurality of radiographic imaging units housed in the plurality of housing portions; and
a storage medium storing instructions and a processor executing the instructions to function as:
an output unit configured to output an image acquired from a plurality of radiographic images based on correspondence information indicating correspondence relationships between the plurality of pieces of identification information and the plurality of detection units by which the plurality of pieces of identification information is detected.

20. The radiographing system according to claim 19,
wherein barcodes are provided on the plurality of radiographic imaging units, respectively, and
wherein the plurality of detection units detects the barcodes on the plurality of radiographic imaging units housed in the plurality of housing portions.

21. The radiographing system according to claim 19, wherein each of the plurality of radiographic imaging units further includes a wireless communication unit configured to wirelessly transmit the radiographic image acquired by each of the plurality of radiographic imaging units.

22. The radiographing system according to claim 19, further comprising connection portions respectively provided to the plurality of housing portions and configured to connect the plurality of radiographic imaging units and a communication unit to each other,
wherein each of the plurality of radiographic imaging units transmits the radiographic image to the communication unit via each of the connection portions.

23. The radiographing system according to claim 19, wherein the processor executes the instructions to further function as a generation unit configured to generate a long-scale image acquired by splicing the plurality of radiographic images based on the correspondence information and path information,
wherein the output unit causes the long-scale image to be displayed on a display unit.

24. The radiographing system according to claim 19, wherein the processor executes the instructions to further function as an image processing unit configured to perform image processing on at least one of the plurality of radiographic images based on the correspondence information and path information.

25. The radiographing system according to claim 19, wherein the processor executes the instructions to further function as a detection unit configured to detect establishment of wired connections of the plurality of radiographic imaging units to a communication unit,
wherein the acquisition unit acquires path information indicating communication paths between the plurality of radiographic imaging units and the communication unit according to the detection of the establishment of the wired connections by the detection unit.

26. The radiographing system according to claim 19, wherein the output unit causes a plurality of images corresponding to the plurality of radiographic images to be displayed in an arranged manner on a display unit.

27. The radiographing system according to claim 19, wherein the output unit outputs the image acquired from the plurality of radiographic images outside.

28. The radiographing system according to claim 19, wherein the output unit further controls display positions of displays indicating the plurality of radiographic imaging units on a display unit based on the correspondence information and path information.

29. A control apparatus for radiographing using a platform including a plurality of housing portions configured to house a plurality of radiographic imaging units configured to acquire a plurality of radiographic images, the control apparatus comprising:
a storage medium storing instructions and a processor executing the instructions to function as:
a reception unit configured to receive a plurality of pieces of identification information of the plurality of radiographic imaging units housed in the plurality of housing portions from a plurality of detection units respectively provided to the plurality of housing portions, and an output unit configured to output an image acquired from the plurality of radiographic images based on correspondence information indicating correspondence relationships between the plurality of pieces of identification information and the plurality of detection units which detect the plurality of pieces of identification information.

30. A control method for controlling a radiographing system including a platform including a plurality of housing portions configured to house a plurality of radiographic imaging units, and a plurality of detection units respectively provided to the plurality of housing portions and configured to detect a plurality of pieces of identification information of the plurality of radiographic imaging units housed in the plurality of housing portions, the control method comprising:

acquiring the plurality of pieces of identification information of the plurality of radiographic imaging units housed in the plurality of housing portions from the plurality of detection units;

acquiring correspondence information indicating correspondence relationships between the plurality of pieces of identification information and the plurality of detection units which detect the plurality of pieces of identification information; and outputting an image acquired from a plurality of radiographic images based on the plurality of pieces of identification information and the correspondence information.

31. A non-transitory computer-readable storage medium storing a program for causing a computer to perform the control method according to claim 30.

* * * * *